(12) United States Patent
Gonzales et al.

(10) Patent No.: US 9,163,200 B2
(45) Date of Patent: Oct. 20, 2015

(54) LIQUID CLEANING AND/OR CLEANSING COMPOSITION

(75) Inventors: Denis Alfred Gonzales, Brussels (BE); Aicha Dkidak, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 532 days.

(21) Appl. No.: 12/972,658

(22) Filed: Dec. 20, 2010

(65) Prior Publication Data

US 2011/0150788 A1 Jun. 23, 2011

Related U.S. Application Data

(60) Provisional application No. 61/288,887, filed on Dec. 22, 2009, provisional application No. 61/326,286, filed on Apr. 21, 2010, provisional application No. 61/326,290, filed on Apr. 21, 2010.

(51) Int. Cl.

| | |
|---|---|
| A61Q 19/10 | (2006.01) |
| A61Q 5/02 | (2006.01) |
| A61Q 11/00 | (2006.01) |
| A61K 8/72 | (2006.01) |
| C11D 3/60 | (2006.01) |
| C11D 17/00 | (2006.01) |
| C11D 3/14 | (2006.01) |
| A61K 8/02 | (2006.01) |
| A61K 8/87 | (2006.01) |
| C11D 3/37 | (2006.01) |

(52) U.S. Cl.
CPC . *C11D 3/14* (2013.01); *A61K 8/025* (2013.01); *A61K 8/87* (2013.01); *A61Q 5/02* (2013.01); *A61Q 11/00* (2013.01); *A61Q 19/10* (2013.01); *C11D 3/37* (2013.01); *C11D 17/0013* (2013.01); *A61K 2800/654* (2013.01)

(58) Field of Classification Search
None
See application file for complete search history.

(56) References Cited

U.S. PATENT DOCUMENTS

| | | |
|---|---|---|
| 1,621,906 A | 3/1927 | Schless |
| 2,082,275 A | 6/1937 | Daimler et al. |
| 2,084,632 A | 6/1937 | Ellis |
| 2,255,082 A | 9/1941 | Orthner et al. |
| 2,438,091 A | 3/1948 | Lynch |
| 2,528,378 A | 10/1950 | Mannheimer |
| 2,658,072 A | 11/1953 | Kosmin |
| 2,702,279 A | 2/1955 | Funderburk et al. |
| 3,070,510 A | 12/1962 | Cooley et al. |
| 3,586,715 A | 6/1971 | Smeets |
| 3,728,075 A * | 4/1973 | Cannan ............ 8/147 |

(Continued)

FOREIGN PATENT DOCUMENTS

| | | |
|---|---|---|
| DE | 24 10 425 A1 | 10/1974 |
| DE | 10 2004 038771 A1 | 8/2005 |

(Continued)

OTHER PUBLICATIONS

International Search Report; International Application No. PCT/US2010/061222; mailed Aug. 9, 2011; 15 pages.

(Continued)

*Primary Examiner* — Brian Gulledge
(74) *Attorney, Agent, or Firm* — Abbey A. Lopez; John T. Dipre (57) ABSTRACT

The present invention relates to a liquid, cleaning and/or cleansing composition comprising abrasive cleaning particles.

10 Claims, 1 Drawing Sheet

(56) References Cited

U.S. PATENT DOCUMENTS

| | | |
|---|---|---|
| 3,812,044 A | 5/1974 | Connor et al. |
| 3,915,903 A | 10/1975 | Wise |
| 3,929,678 A | 12/1975 | Laughlin et al. |
| 3,985,668 A | 10/1976 | Hartman |
| 4,025,444 A * | 5/1977 | Murphy et al. ............... 510/332 |
| 4,051,056 A | 9/1977 | Hartman |
| 4,088,620 A | 5/1978 | Nihongi et al. |
| 4,102,992 A | 7/1978 | Davis |
| 4,240,919 A | 12/1980 | Chapman |
| 4,298,490 A | 11/1981 | Lange et al. |
| 4,309,316 A | 1/1982 | Lange et al. |
| 4,473,611 A | 9/1984 | Haq |
| 4,481,126 A | 11/1984 | Trinh et al. |
| 4,537,604 A * | 8/1985 | Dawson ......................... 51/298 |
| 4,565,644 A | 1/1986 | Smith et al. |
| 4,565,647 A | 1/1986 | Llenado |
| 4,581,385 A * | 4/1986 | Smith et al. .................. 521/111 |
| 4,657,692 A | 4/1987 | Choy et al. |
| 4,663,069 A | 5/1987 | Llenado |
| 4,676,920 A | 6/1987 | Culshaw |
| 4,704,233 A | 11/1987 | Hartman et al. |
| 4,767,563 A | 8/1988 | De Buzzaccarini |
| 4,772,425 A | 9/1988 | Chirash et al. |
| 4,842,763 A | 6/1989 | Troger et al. |
| 4,906,396 A | 3/1990 | Falholt et al. |
| 5,059,414 A * | 10/1991 | Dallal et al. ................. 424/70.2 |
| 5,287,207 A | 2/1994 | Mulkens et al. |
| 5,500,451 A | 3/1996 | Goldman et al. |
| 5,679,326 A * | 10/1997 | Bara et al. .................... 424/70.1 |
| 5,776,872 A | 7/1998 | Giret et al. |
| 5,776,878 A | 7/1998 | Theon |
| 5,798,505 A | 8/1998 | Lee |
| 5,821,214 A | 10/1998 | Weibel |
| 5,830,445 A | 11/1998 | Bouillon et al. |
| 5,883,062 A | 3/1999 | Addison et al. |
| 5,898,026 A | 4/1999 | Yianakopoulos et al. |
| 5,906,973 A | 5/1999 | Ouzounis et al. |
| 6,008,181 A | 12/1999 | Cripe et al. |
| 6,020,303 A | 2/2000 | Cripe et al. |
| 6,060,443 A | 5/2000 | Cripe et al. |
| 6,080,707 A | 6/2000 | Glenn et al. |
| 6,132,212 A | 10/2000 | Horiguchi et al. |
| 6,172,018 B1 * | 1/2001 | Mueller et al. ............... 510/125 |
| 6,221,829 B1 | 4/2001 | Symes et al. |
| 6,242,405 B1 | 6/2001 | Lykke et al. |
| 6,265,363 B1 | 7/2001 | Viscovitz |
| 6,268,325 B1 | 7/2001 | Luciani et al. |
| 6,274,540 B1 | 8/2001 | Scheibel et al. |
| 6,299,746 B1 | 10/2001 | Conte et al. |
| 6,306,817 B1 | 10/2001 | Kott et al. |
| 6,359,031 B1 | 3/2002 | Lykke et al. |
| 6,369,121 B1 | 4/2002 | Catalfamo et al. |
| 6,444,716 B1 | 9/2002 | Hird et al. |
| 6,514,926 B1 | 2/2003 | Kott et al. |
| 6,525,233 B1 | 2/2003 | Connor et al. |
| 6,537,957 B1 | 3/2003 | Cardola et al. |
| 6,566,319 B1 | 5/2003 | Scheibel et al. |
| 6,583,096 B1 | 6/2003 | Kott et al. |
| 6,593,285 B1 | 7/2003 | Scheibel et al. |
| 6,602,840 B1 | 8/2003 | Scheibel et al. |
| 6,699,963 B2 | 3/2004 | Noda et al. |
| 6,749,066 B2 | 6/2004 | Bergman |
| 6,759,377 B2 | 7/2004 | Hackenthal et al. |
| 6,767,878 B1 | 7/2004 | Paye et al. |
| 6,808,759 B1 | 10/2004 | Okumura et al. |
| 6,858,216 B2 | 2/2005 | Schulze zur Wiesche et al. |
| 7,307,055 B2 | 12/2007 | Cook et al. |
| 7,393,820 B2 | 7/2008 | Soldanski et al. |
| 7,713,921 B2 | 5/2010 | Boutique et al. |
| 7,994,111 B2 | 8/2011 | Caggioni et al. |
| 2002/0137647 A1 | 9/2002 | Hackenthal et al. |
| 2002/0166832 A1 | 11/2002 | Silud et al. |
| 2002/0173243 A1 | 11/2002 | Costas et al. |
| 2003/0176633 A1 | 9/2003 | Noda et al. |
| 2003/0215417 A1 | 11/2003 | Uchiyama et al. |
| 2004/0216388 A1 | 11/2004 | Mathur et al. |
| 2004/0266645 A1 | 12/2004 | Albrecht et al. |
| 2005/0065056 A1 | 3/2005 | Cook et al. |
| 2005/0130873 A1 * | 6/2005 | Cheung et al. ................. 510/507 |
| 2005/0170979 A1 | 8/2005 | Massaro et al. |
| 2005/0201965 A1 | 9/2005 | Kuhlman et al. |
| 2006/0011885 A1 | 1/2006 | Christmas et al. |
| 2006/0094635 A1 | 5/2006 | Pereira |
| 2006/0177488 A1 * | 8/2006 | Caruso et al. ................. 424/443 |
| 2007/0006391 A1 | 1/2007 | Ghosh et al. |
| 2007/0010415 A1 | 1/2007 | Kinscherf et al. |
| 2007/0041927 A1 | 2/2007 | Blaeser et al. |
| 2007/0043147 A1 | 2/2007 | Higgins et al. |
| 2007/0135645 A1 | 6/2007 | Ignatyev et al. |
| 2007/0138671 A1 | 6/2007 | Anastasiou et al. |
| 2007/0167345 A1 | 7/2007 | Soldanski et al. |
| 2007/0191256 A1 | 8/2007 | Fossum et al. |
| 2007/0270730 A1 | 11/2007 | Rische et al. |
| 2008/0108714 A1 | 5/2008 | Swazey et al. |
| 2008/0139433 A1 | 6/2008 | Mock et al. |
| 2008/0139702 A1 | 6/2008 | De Almeida et al. |
| 2008/0149137 A1 | 6/2008 | Steinbrenner et al. |
| 2008/0248144 A1 | 10/2008 | Guenter et al. |
| 2009/0176935 A1 | 7/2009 | Boeckh et al. |
| 2009/0253816 A1 | 10/2009 | Nascimento et al. |
| 2009/0291306 A1 | 11/2009 | Quadbeck-Seeger |
| 2009/0325837 A1 | 12/2009 | Mundschau et al. |
| 2010/0081604 A1 | 4/2010 | Barger et al. |
| 2010/0081605 A1 | 4/2010 | Barger et al. |
| 2010/0081606 A1 | 4/2010 | Barger et al. |
| 2010/0197553 A1 | 8/2010 | Barnabas et al. |
| 2011/0021398 A1 | 1/2011 | Allef et al. |
| 2011/0039744 A1 | 2/2011 | Heath et al. |
| 2011/0150787 A1 | 6/2011 | Gonzales et al. |
| 2011/0150788 A1 | 6/2011 | Gonzales et al. |
| 2011/0150949 A1 | 6/2011 | Gonzales et al. |
| 2011/0150950 A1 | 6/2011 | Gonzales et al. |
| 2011/0150951 A1 | 6/2011 | Gonzales et al. |
| 2011/0178196 A1 | 7/2011 | Steinke et al. |
| 2011/0189414 A1 | 8/2011 | Whitehouse |
| 2011/0262371 A1 | 10/2011 | Deleersnyder et al. |
| 2011/0262504 A1 | 10/2011 | Deleersnyder et al. |
| 2011/0287105 A1 | 11/2011 | Gittleman |
| 2012/0029519 A1 | 2/2012 | Sengun et al. |
| 2012/0066851 A1 | 3/2012 | Gonzales et al. |
| 2012/0071378 A1 | 3/2012 | Gonzales et al. |
| 2012/0071379 A1 | 3/2012 | Gonzales et al. |
| 2012/0071380 A1 | 3/2012 | Gonzales et al. |
| 2012/0071383 A1 | 3/2012 | Perez-Prat Vinuesa et al. |
| 2012/0202730 A1 | 8/2012 | Allef et al. |

FOREIGN PATENT DOCUMENTS

| | | |
|---|---|---|
| DE | 10 2005 023801 A1 | 11/2006 |
| EP | 0 226 723 A2 | 7/1987 |
| EP | 0 957 156 A1 | 11/1999 |
| EP | 1 136 063 A2 | 9/2001 |
| EP | 1 460 125 A1 | 9/2004 |
| GB | 2 001 099 A | 1/1979 |
| GB | 2 126 999 A | 4/1984 |
| GB | 2 145 729 A | 4/1985 |
| GB | 2 184 454 A | 6/1987 |
| JP | A-S54-154410 | 12/1979 |
| JP | 59192526 A | 10/1984 |
| JP | 10025239 A | 1/1998 |
| JP | 2005 296822 A | 10/2005 |
| JP | 2007 077311 A | 3/2007 |
| JP | 2009 160717 A | 7/2009 |
| WO | WO 91/14420 A1 | 10/1991 |
| WO | WO 99/05084 A1 | 2/1999 |
| WO | WO 99/52500 A1 | 10/1999 |
| WO | WO 01/09279 A1 | 2/2001 |
| WO | WO 01/30315 A1 | 5/2001 |
| WO | WO 01/31110 A1 | 5/2001 |
| WO | WO 02/38720 A1 | 5/2002 |
| WO | WO 03/043599 A1 | 5/2003 |
| WO | WO 2004/071483 A1 | 8/2004 |

(56) References Cited

FOREIGN PATENT DOCUMENTS

| WO | WO 2004/083328 A2 | 9/2004 |
|---|---|---|
| WO | WO 2008/006736 A1 | 1/2008 |
| WO | WO 2008/109270 A1 | 9/2008 |

OTHER PUBLICATIONS

European Search Report, Application No. 10195921.1-1221, Dated Sep. 15, 2011, 12 pages.
U.S. Appl. No. 13/517,837, filed Jun. 14, 2012, Gonzales, et al.
U.S. Appl. No. 13/517,728, filed Jun. 14, 2012, Gonzales, et al.
U.S. Appl. No. 13/526,592, filed Jun. 19, 2012, Gonzales, et al.
U.S. Appl. No. 13/526,596, filed Jun. 19, 2012, Gonzales, et al.
U.S. Appl. No. 13/517,746, filed Jun. 14, 2012, Gonzales, et al.
U.S. Appl. No. 13/526,605, filed Jun. 19, 2012, Gonzales, et al.
U.S. Appl. No. 13/526,613, filed Jun. 19, 2012, Gonzales, et al.
U.S. Appl. No. 13/517,762, filed Jun. 14, 2012, Perez-Prat Vinuesa, et al.
U.S. Appl. No. 13/621,858, filed Sep. 18, 2012, Gonzales, et al.
U.S. Appl. No. 13/621,860, filed Sep. 18, 2012, Perez-Prat Vinuesa, et al.
ASTM Designation: F1877-05 Jun. 10, 2009; Standard Practice for Characterization of Particles; 14 pages; chapter 11.3.6; Section 11.3.2.
International Standard; ISO 9276-6:2008(E) section 8.2; section 7; Representation of results of particle size analysis—Part 6: Descriptive and quantitative representation of particle shape and morphology.
"Vegetable Ivory", W.P. Armstrong, (http://waynesword.palomar.edu/p1jan99.htm), 2012.
"Phytelephas", Wikipedia.org (http://en.wikipedia.org/wiki/Phytelephas), 2012.

\* cited by examiner

LIQUID CLEANING AND/OR CLEANSING COMPOSITION

CROSS REFERENCE TO RELATED APPLICATION

This application claims the benefit of U.S. Provisional Application No. 61/288,887 filed Dec. 22, 2009, of U.S. Provisional Application No. 61/326,286, filed Apr. 21, 2010 and of U.S. Provisional Application No. 61/326,290, filed Apr. 21, 2010.

TECHNICAL FIELD

The present invention relates to liquid compositions for cleaning and/or cleansing a variety of inanimate and animate surfaces, including hard surfaces in and around the house, dish surfaces, hard and soft tissue surface of the oral cavity, such as teeth, gums, tongue and buccal surfaces, human and animal skin, car and vehicles surfaces, etc. More specifically, the present invention relates to liquid scouring composition comprising suitable particles for cleaning and/or cleansing.

BACKGROUND OF THE INVENTION

Scouring compositions such as particulate compositions or liquid (incl. gel, paste-type) compositions containing abrasive components are well known in the art. Such compositions are used for cleaning and/or cleansing a variety of surfaces; especially those surfaces that tend to become soiled with difficult to remove stains and soils.

Amongst the currently known scouring compositions, the most popular ones are based on abrasive particles with shapes varying from spherical to irregular. The most common abrasive particles are either inorganic like carbonate salt, clay, silica, silicate, shale ash, perlite and quartz sand or organic polymeric beads like polypropylene, PVC, melamine, urea, polyacrylate and derivatives, and come in the form of liquid composition having a creamy consistency with the abrasive particles suspended therein.

The surface safety profile of such currently known scouring compositions is inadequate alternatively, poor cleaning performances are shown for compositions with an adequate surface safety profile. Indeed, due to the presence of very hard abrasive particles, these compositions can damage, i.e., scratch, the surfaces onto which they have been applied. Indeed, the formulator needs to choose between good cleaning/cleansing performance but featuring strong surface damage or compromising on the cleaning/cleansing performance while featuring acceptable surface safety profile. In addition, such currently known scouring compositions at least in certain fields of application (e.g., hard surface cleaning) are perceived by consumers as outdated.

It is thus an objective of the present invention to provide a liquid cleaning and/or cleansing composition suitable to clean/cleanse a variety of surfaces, including inanimate and animate surfaces, such hard surfaces in and around the house, dish surfaces, hard and soft tissue surface of the oral cavity, such as teeth, gums, tongue and buccal surfaces, human and animal skin, etc., wherein the composition provides good cleaning/cleansing performance, whilst providing a good surface safety profile.

It has been found that the above objective can be met by the composition according to the present invention.

It is an advantage of the compositions according to the present invention that they may be used to clean/cleanse inanimate and animate surfaces made of a variety of materials like glazed and non-glazed ceramic tiles, enamel, stainless steel, Inox®, Formica®, vinyl, no-wax vinyl, linoleum, melamine, glass, plastics, painted surfaces, human and animal skin, hair, hard and soft tissue surface of the oral cavity, such as teeth, gums, tongue and buccal surfaces, and the like.

A further advantage of the present invention is that in the compositions herein, the particles can be formulated at very low levels, whilst still providing the above benefits. Indeed, in general for other technologies, high levels of abrasive particles are needed to reach good cleaning/cleansing performance, thus leading to high formulation and process cost, difficult rinse and end cleaning profiles, as well as limitation for aesthetics and a pleasant hand feel of the cleaning/cleansing composition.

SUMMARY OF THE INVENTION

A liquid cleaning and/or cleansing composition comprising abrasive cleaning particles, wherein said abrasive cleaning particles have a packing density between 10 kg/m$^3$ and 250 kg/m$^3$ and wherein said abrasive cleaning particles have a HV Vickers hardness from 3 to 50 kg/mm$^2$.

The present invention further encompasses a process of cleaning and/or cleansing a surface with a liquid, cleaning and/or cleansing composition comprising abrasive cleaning particles, wherein said surface is contacted with said composition, preferably wherein said composition is applied onto said surface.

DETAILED DESCRIPTION OF THE INVENTION

The Liquid Cleaning/Cleansing Composition

The compositions according to the present invention are designed as cleaners/cleansers for a variety of inanimate and animate surfaces. Preferably, the compositions herein are suitable for cleaning/cleansing surfaces selected from the group consisting of inanimate surfaces, animate surfaces.

In a preferred embodiment, the compositions herein are suitable for cleaning/cleansing inanimate surfaces selected from the group consisting of household hard surfaces; dish surfaces; surfaces like leather or synthetic leather; and automotive vehicles surfaces.

In a highly preferred embodiment, the compositions herein are suitable to clean household hard surfaces.

By "household hard surface", it is meant herein any kind of surface typically found in and around houses like kitchens, bathrooms, e.g., floors, walls, tiles, windows, cupboards, sinks, showers, shower plastified curtains, wash basins, WCs, fixtures and fittings and the like made of different materials like ceramic, vinyl, no-wax vinyl, linoleum, melamine, glass, Inox®, Formica®, any plastics, plastified wood, metal or any painted or varnished or sealed surface and the like. Household hard surfaces also include household appliances including, but not limited to refrigerators, freezers, washing machines, automatic dryers, ovens, microwave ovens, dishwashers and so on. Such hard surfaces may be found both in private households as well as in commercial, institutional and industrial environments.

By "dish surfaces" it is meant herein any kind of surfaces found in dish cleaning, such as dishes, cutlery, cutting boards, pans, and the like. Such dish surfaces may be found both in private households as well as in commercial, institutional and industrial environments.

In an another preferred embodiment, the compositions herein are suitable for cleaning/cleansing animate surfaces selected from the group consisting of human skin; animal skin; human hair; animal hair; and teeth.

The compositions according to the present invention are liquid compositions as opposed to a solid or a gas. Liquid compositions include compositions having a water-like viscosity as well as thickened compositions, such as gels and pastes.

In a preferred embodiment herein, the liquid compositions herein are aqueous compositions. Therefore, they may comprise from 65% to 99.5% by weight of the total composition of water, preferably from 75% to 98% and more preferably from 80% to 95%.

In another preferred embodiment herein, the liquid compositions herein are mostly non-aqueous compositions although they may comprise from 0% to 10% by weight of the total composition of water, preferably from 0% to 5%, more preferably from 0% to 1% and most preferably 0% by weight of the total composition of water.

In a preferred embodiment herein, the compositions herein are neutral compositions, and thus have a pH, as is measured at 25° C., of 6-8, more preferably 6.5-7.5, even more preferably 7.

In other preferred embodiment compositions have pH preferably above pH 4 and alternatively have pH preferably below pH 9.

Accordingly, the compositions herein may comprise suitable bases and acids to adjust the pH.

A suitable base to be used herein is an organic and/or inorganic base. Suitable bases for use herein are the caustic alkalis, such as sodium hydroxide, potassium hydroxide and/or lithium hydroxide, and/or the alkali metal oxides such as sodium and/or potassium oxide or mixtures thereof. A preferred base is a caustic alkali, more preferably sodium hydroxide and/or potassium hydroxide.

Other suitable bases include ammonia, ammonium carbonate, all available carbonate salts such as $K_2CO_3$, $Na_2CO_3$, $Ca_2CO_3$, $Mg_2CO_3$, etc., alkanolamines (as e.g. monoethanolamine), urea and urea derivatives, polyamine, etc.

Typical levels of such bases, when present, are of from 0.01% to 5.0% by weight of the total composition, preferably from 0.05% to 3.0% and more preferably from 0.1% to 0.6%.

The compositions herein may comprise an acid to trim its pH to the required level, despite the presence of an acid, if any, the compositions herein will maintain their preferred neutral pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and a mixture thereof. A mixture of said acids may be commercially available from BASF under the trade name Sokalan® DCS. A suitable inorganic acid is selected from the group consisting hydrochloric acid, sulphuric acid, phosphoric acid and a mixture thereof.

A typical level of such an acid, when present, is of from 0.01% to 5.0% by weight of the total composition, preferably from 0.04% to 3.0% and more preferably from 0.05% to 1.5%.

In a preferred embodiment according to the present invention the compositions herein are thickened compositions. Preferably, the liquid compositions herein have a viscosity of up to 7500 cps at $20 \text{ s}^{-1}$, more preferably from 5000 cps to 50 cps, yet more preferably from 2000 cps to 50 cps and most preferably from 1500 cps to 300 cps at $20 \text{ s}^{-1}$ and 20° C. when measured with a Rheometer, model AR 1000 (Supplied by TA Instruments) with a 4 cm conic spindle in stainless steel, 2° angle (linear increment from 0.1 to 100 $\sec^{-1}$ in max. 8 minutes).

In another preferred embodiment according to the present invention the compositions herein have a water-like viscosity. By "water-like viscosity" it is meant herein a viscosity that is close to that of water. Preferably the liquid compositions herein have a viscosity of up to 50 cps at 60 rpm, more preferably from 0 cps to 30 cps, yet more preferably from 0 cps to 20 cps and most preferably from 0 cps to 10 cps at 60 rpm and 20° C. when measured with a Brookfield digital viscometer model DV II, with spindle 2.

Abrasive Cleaning Particles

The applicant has surprisingly discovered that efficient cleaning result can be achieved with particle population occupying a large volume per mass of particles loaded in a cleaning composition. The volume that the particles will occupy is defined by the packing density of the particles. The packing density of a particle population represents the mass of a sample of particle population divided by the volume occupied by the particles sample measured in dry condition after packing with normal gravity force. Incidentally, a particle population with low packing density will occupy a high volume, both in cleaner and during cleaning operation to provide effective cleaning performance, while a particle sample with high packing density will occupy a low volume, both in cleaner and during cleaning operation hence providing low effective cleaning performance.

Indeed, particles with low packing density are effective at providing maximum contact area between the abrasive particles and the soil and/or surface to be cleaned. And therefore, lower quantity of abrasive particles can be used in cleaning composition i.e., below 10% vs. commonly above 20%, while delivering equal or better cleaning effectiveness. It is commonly known that higher quantity of particles in the cleaning composition leads to a better cleaning effectiveness, additionally a higher mass of particle was used to maximize the cleaning performance. The applicant has established that the cleaning efficiency is rather impacted by the volume that the abrasive population occupies at the cleaning interface versus typically the mass of the abrasive population. Incidentally, particles with low packing density typically require lower mass load of the abrasive in the cleaner versus high packing density particles to produce efficient cleaning.

Typical abrasive cleaning particles have granular to spherical shape made of plain material e.g.: featuring either high intrinsic material density in addition to featuring low/no porosity that would minimize the packing density. There is an exception with few mineral-based abrasives (e.g.: perlite or pumice, etc.), which despite featuring a low packing density, due to their expanded structures, are inadequate for most of the general cleaning tasks because of their high hardness, which promotes surface damage. Incidentally the commonly used abrasive particles in cleaning compositions have packing density above 400 kg/m$^3$ and are poorly efficient from a volume-occupancy/mass viewpoint and incidentally feature low cleaning efficiency.

Packing Density of Abrasive Particles

Surprisingly, the applicant has discovered that cleaning particles having packing density (Packing density test method is described below) ranging from 50 to 250 kg/m$^3$ are delivering exceptional cleaning performance. It is understood that the packing density incorporates critical intrinsic information of the cleaning particles, which are otherwise known to have an impact on the cleaning performance, such as particle size and particle shape. However, the packing density also includes mass-efficient information, since it additionally takes into account the density of the raw material of the particle. Furthermore, in addition to excellent cleaning performances, the combination of the low packing density and accurately selected particle hardness range of the cleaning particles allow delivery of excellent surface safety profile.

The applicant has found that abrasive population with high packing density feature low cleaning performance while, on the other hand, abrasive population with excessive low packing density has intrinsic fragility that is also inadequate for cleaning purpose via mechanical abrasion. Incidentally, the applicant has found out that the abrasive cleaning particles having a packing density from 10 kg/m$^3$ to 250 kg/m$^3$, preferably from 50 kg/m$^3$ to 150 kg/m$^3$, more preferably from 70 kg/m$^3$ to 120 kg/m$^3$ are proving improved cleaning performance and surface safety.

Packing Density Test Method:

One tenth of a gram (0.1 g+/−0.001 g) of dry particles is placed into a 20 ml precise metric graduated Pyrex® volumetric cylinder (as available from Sigma-Aldrich). The cylinder is sealed (e.g. with a stopper or film), and subsequently shaken using a Vortex mixer (for example, the model L-46 Power Mix from Labinco DNTE SP-016) at 2500 rpm (maximum speed) for 30 seconds. The volume of the particles is measured after vibration. If the volume is between 5 to 15 ml, this is converted accordingly into packing density as expressed in kg/m3. If the volume of 0.1 g is less than 5 ml, then two tenths of a gram (0.2 g+/−0.001 g) of dry particles is used to re-run the test in clean cylinder. If the volume of the 0.2 g is less than 5 ml, then half a gram (0.5 g+/−0.001 g) of dry particles is used to re-run the test in a clean cylinder. If the volume of the 0.5 g is less than 5 ml, then one gram (1.0 g+/−0.001 g) of dry particles is used to re-run the test in a clean cylinder, with volumes between 3 to 15 ml converted into kg/m3 for packing density.

Hardness of the Abrasive Particles:

Preferred abrasive cleaning particles suitable for used herein are hard enough to provide good cleaning/cleansing performance, whilst providing a good surface safety profile.

The hardness of the abrasive particles reduced from the foam can be modified by changing the raw material used to prepare the foam. For example modification of the hardness of the polyurethane foam is possible via several ways. For example, without being exhaustive, the selection of the diisocyanate and especially the selection of the isocyanate with high functionality e.g.: >2, preferably >2.5, most preferably above 2.7, increases the polyurethane hardness. Similarly, the use of low molecular weight polyols e.g.: <4000 Mw, preferably <2000 Mw and most preferably below 1000 Mw also increase the polyurethane hardness. More importantly is the balance diisocyanate/polyols in the reaction mixture, although excess of diisocyanate also increase the foam hardness. Another possibility to increase hardness is to introduce a small molecular weight crosslinker. Alternatively selection of catalyst will promote the formation of urea bond, is additional way to increase the foam hardness.

Preferred abrasive cleaning particles in the present invention have hardness from 3 to 50 kg/mm$^2$, preferably from 4 to 25 kg/mm$^2$ and most preferably from 5 to 15 kg/mm$^2$ on the HV Vickers hardness.

Vickers Hardness Test Method:

Vickers hardness HV is measured at 23° C. according to standard methods ISO 14577-1, ISO 14577-2, ISO 14577-3. The Vickers hardness is measured from a solid block of the raw material at least 2 mm in thickness. The Vickers hardness micro indentation measurement is carried out by using the Micro-Hardness Tester (MHT), manufactured by CSM Instruments SA, Peseux, Switzerland.

As per the ISO 14577 instructions, the test surface should be flat and smooth, having a roughness (Ra) value less than 5% of the maximum indenter penetration depth. For a 200 µm maximum depth this equates to a Ra value less than 10 µm. As per ISO 14577, such a surface may be prepared by any suitable means, which may include cutting the block of test material with a new sharp microtome or scalpel blade, grinding, polishing or by casting melted material onto a flat, smooth casting form and allowing it to thoroughly solidify prior testing.

Suitable general settings for the Micro-Hardness Tester (MHT) are as follows:
Control mode: Displacement, Continuous
Maximum displacement: 200 µm
Approach speed: 20 nm/s
Zero point determination: at contact
Hold period to measure thermal drift at contact: 60 s
Force application time: 30 s
Frequency of data logging: at least every second
Hold time at maximum force: 30 s
Force removal time: 30 s
Shape/Material of intender tip: Vickers Pyramid Shape/Diamond Tip Alternatively, the abrasive cleaning particles in the present invention hardness may also be expressed according to the MOHS hardness scale. Preferably, the MOHS hardness is comprised between 0.5 and 3.5 and most preferably between 1 and 3. The MOHS hardness scale is an internationally recognized scale for measuring the hardness of a compound versus a compound of known hardness, see Encyclopedia of Chemical Technology, Kirk-Othmer, 4 th Edition Vol 1, page 18 or Lide, D.R (ed) CRC Handbook of Chemistry and Physics, 73 rd edition, Boca Raton, Fla.: The Rubber Company, 1992-1993. Many MOHS Test kits are commercially available containing material with known MOHS hardness. For measurement and selection of abrasive material with selected MOHS hardness, it is recommended to execute the MOHS hardness measurement with un-shaped particles e.g.: with spherical or granular forms of the abrasive material since MOHS measurement of shape particles will provide erroneous results.

Size of the Abrasive Particles:

In a preferred embodiment, the abrasive cleaning particles have a mean ECD from 10 µm to 1000 µm, preferably from 50 µm to 500 µm, more preferably from 100 µm to 350 µm and most preferably from 150 to 250 µm.

Indeed, the Applicant has found that the abrasive particle size can be critical to achieve efficient cleaning performance, whereas excessively abrasive population with small particle sizes e.g.: typically below 10 micrometers feature polishing action vs. cleaning despite featuring a high number of particles per particle load in cleaner inherent to the small particle size. On the other hand, abrasive population with excessively high particle size, e.g.: typically above 1000 micrometers, delivers not optimal cleaning efficiency since the number of particles per particle load in cleaner decreases significantly inherently to the large particle size. Additionally, excessively small particle sizes are not desirable in cleaner/for cleaning task since in practice, small and numerous particles are often hard to remove from the various surface topologies which require excessive effort to remove from the user unless leaving the surface with visible particles residue. On the other hand, excessively large particle are too easily detected visually or provide bad tactile experience while handling or using the cleaner. Therefore, the applicants define herein an optimal particle size range which delivers both optimal cleaning performance and usage experience.

The abrasive particles have size defined by their area-equivalent diameter (ISO 9276-6:2008(E) section 7) also called Equivalent Circle Diameter ECD (ASTM F1877-05 Section 11.3.2). Mean ECD of particle population is calculated as the average of respective ECD of each particles of a particle population of at least 10 000 particles, preferably above 50 000 particles, more preferably above 100 000 particles after excluding from the measurement and calculation the data of particles having area-equivalent diameter (ECD) of below 10 micrometers. Mean data are extracted from volume-based vs. number-based measurements.

In one preferred example, the size of the abrasive cleaning particles used in the present invention is modified during usage especially undergoing significant size reduction. Hence the particle remain visible or tactile detectable in liquid composition and at the start of the usage process to provide effective cleaning. As the cleaning process progresses, the abrasive particles disperse or break into smaller particles and become invisible to an eye or tactile undetectable.

It has surprisingly been found that the abrasive cleaning particles of the present invention show a good cleaning performance even at relatively low levels, such as preferably from 0.1% to 20% by weight of the total composition of said abrasive cleaning particles, preferably from 0.1% to 10%, more preferably from 0.5% to 5%, even more preferably from 0.5% to 2%.

The particles used in the present invention can be white, transparent or colored by use of suitable dyes and/or pigments. Additionally suitable color stabilizing agents can be used to stabilize desired color. The abrasive particles are preferable color stable particles.

In one preferred example, the abrasive cleaning particles used in the present invention remain visible when liquid composition is stored into a bottle while during the effective cleaning process abrasive particles disperse or break into smaller particles and become invisible to an eye.

Low-packing density abrasive with adequate HV Vickers hardness can be produced by careful selection or preparation of material derived from vegetable sources, mineral sources or from organic/polymeric synthesis and mix thereof.

Typical material from vegetable sources are preferably derived from wood, rice, corn cob, palm biomass, bamboo, kenaf, etc. whereas specific fibrous or spongy species are particularly preferred due to their inherent natural low density. Typical examples are Arcobel, Lignocel or Rheofix from Rettenmeir or Kenaf powder from EngageNRC.

A particularly suitable mean to achieve low packing density abrasive particles is to expand the abrasive material with gas e.g.: via a foaming process. Low packing density mineral or vegetable based abrasive can be achieved by mixing the mineral or vegetable matter—available in fine particle—e.g.: preferably below 50 micrometers, and more preferably below 10 micrometers particle size into a foaming process with solidifying agents. In most simple and common case, the abrasive raw material per se—e g.: mineral or non-mineral filler—is dispersed within a matrix prior to undergoing the foaming process to achieve the adequate foam structure. In that case, the material used as filler in foaming processes is typically—without being exhaustive—e.g.: organic or inorganic salt abrasives such as carbonate-derived salts, phosphate-derived salts, pyrophosphate-derived salts, silica or alumina derived salts, diatomaceous, fuller earth, talk, etc., polymeric material derived from following structures e.g.: polyethylene, polypropylene, PVC, polycarbonate, melamine, urea, polyurethane, polyacrylate, polystyrene, phenolic, polyesters, polyamide, or natural material derived from cellulose, lingo-cellulose or shell such as nut shell, kernel, wood, bamboo, plants, etc.

Preferably the abrasive particles are made from the polymeric material selected from the group consisting of polyethylene, polypropylene, PVC, polycarbonate, melamine, urea, polyurethane, polyacrylate, polystyrene, phenolic, polyesters, polyamide and mixtures thereof and natural abrasives derived from cellulose, lingo-cellulose or shell such as nut shell, apple seeds, olive stones, apricot seed, kernel, wood, bamboo and plants and mixtures thereof. More preferably the abrasive particles are made polymeric material selected from the group consisting of polyethylene, polypropylene, PVC, polycarbonate, melamine, urea, polyurethane, polyacrylate, polystyrene, phenolic, polyesters, polyamide and mixtures thereof. Even more preferably the abrasive particles are made from the polymeric material selected from the group consisting of polyurethane, polyester, polyacrylate, polystyrene and mixtures thereof. Most preferably the abrasive particles are made from the rigid polyurethane made from the diisocyanate (e.g. Lupranate M200R or Lupranate M20S) and diol (Lupranol 3423).

In a preferred embodiment, low packing density material is synthetic and is produced from foamed or expanded organic or polymeric material used without filler. The particles of the present invention having packing density within desired target range are reduced in particles with typical grinding or milling processes from the foamed or expanded material. Other suitable means for reducing the foamed or expanded material into abrasive particles include the use of eroding tools, such as a high speed eroding wheel with dust collector wherein the surface of the wheel is engraved with a pattern or is coated with abrasive sandpaper or the like to form the abrasive cleaning particles herein.

In a preferred embodiment the abrasive particles are obtained from a foam by reducing (preferably by grinding or milling) the foam into abrasive particles. More preferably the abrasive particles are obtained from foamed polymeric material, wherein polymeric material is selected from the group consisting of polyethylene, polypropylene, PVC, polycarbonate, melamine, urea, polyurethane, polyacrylate, polystyrene, phenolic, polyesters, polyamide and mixtures thereof. Even more preferably the abrasive particles are obtained from foamed polymeric material selected from the group consisting of polyurethane, polyester, polyacrylate, polystyrene and mixtures thereof. Most prefereably the abrasive particles are obtained from rigid polyurethane foam made from the diisocyanate (e.g. Lupranate M200R or Lupranate M20S) and diol (Lupranol 3423).

Foaming and/or expanding processes of the raw material into a foam structure are typically achieved via gas expansion process. Gas expansion process can happen either by injecting gas or solvent within the abrasive precursor or allowing expansion by pressure drop and/or increase of temperature, e.g.: extrusion foaming process. In extrusion process, a thermoplastic material in a form of pure polymer or polymer blend or plasticized polymers is usually used. Examples of thermoplastic polymers are polyethylene, polypropylene, PVC, polycarbonate, polyurethane, polyacrylate, polystyrene, polyesters, polyamide and mixtures thereof. An abundant list of alternative thermoplastic polymers exists on extrusion foaming or gas foaming literature (for examples see book "Thermoplastic Foam Extrusion" from James L. Throne or "Foam Extrusion: Principles and Practice from Shau-Tarng Lee). Typical gases used in such processes are air, nitrogen, carbon dioxide or organic solvent such as pentane, cyclopentane and mixtures thereof with or without nucleation and foam stabilizing agents. In most cases, a controlled amount of gas is allowed to dissolve into the polymer/polymeric mixture into melted phase, whereas the skilled operator can control accurately the foaming parameters e.g.: formulation, time/ temperature/pressure cycle parameters to target specific foam structures.

Foaming processes and foam structures are also typically achieved via emulsion foaming of monomers followed by a hardening step via chemical, heat or radiative e.g.: UV curing and if necessary followed by a drying step of the solidified foam. Much monomers types are possible to use e.g.: derived from non-exhaustive list of following monomer structures e.g.: vinyl, styrene, acrylate, metacrylate, diene, etc. Examples of materials, foaming and curing process are extensively described in literature (e.g.: refer to book "Emulsion Polymer Technology" from Robert D. Athey). A preferred route for production of the foam is to form a water/oil high internal phase emulsion of water in the monomer mixture and polymerize in-situ, as described in U.S. Pat. No. 6,369,121 to Catalfamo et al. In a preferred embodiment the foam is produced after polymerization of a divinyl benzene cross-linked styrene polymer with water/oil high internal phase emulsion process which after curing is afterward reduced to particles via a grinding or milling operation.

Foaming processes and foam structures are typically achieved by mechanical agitation e.g.; battering of a viscous mix e.g.: typically including protein with emulsifying and possibly stabilizing features followed by a step of curing/ hardening and if necessary drying of the solidified foam. Non-exhaustive examples of proteins are white egg or pure albumen, gelatin, saponin, gluten, soybean protein, globulin, prolamine, glutelin, histone, protamine and mixtures thereof. The protein is often agitated in presence of water, emulsifying agent, stabilizers e.g.: alginic acid, and much desirably a significant amount of polymerizable monomer and/ crosslinker to achieve sufficient hardness of the foam. For further reference refer to book "Functionality of Proteins in Food" from Joseph F. Zayas, "Protein Functionality in Food Systems" from Hettiarachchy, Article in Journal of Cereal science 47 (2008) 233-238 from E.Zukowska et Al; or US2006/0065159.

Particularly preferred foaming processes and foam structures are typically achieved by simultaneous polymerization with or without cross linking of monomers with in-situ production of expanding gas such as typical processes used to produce polyurethane foam. Processes, polyurethane precursors, formulations, additives, etc. are abundantly described in literature as well as, most conveniently, their incidence on the various critical foam structure parameters such as foam density, cell size, content of closed cell, strut aspect ratio and to some extent foam and particle hardness which are the object of the present invention so to produce effective shapes of cleaning particles. Much information on polyurethane formulation and production processes is available in literature (see for reference following books: "Rigid polyurethane/polyisocyanurate foam processing" from Robert Wood "Polyurethane and Related Foams: Chemistry and Technology" from Kaneyoshi Ashida and "Chemistry and technology of polyols for polyurethanes" from Mihail Ionescu).

The applicant has found out that good cleaning particle featuring low packing density can be produced from foams with very specific structure parameters as described herein later on. Indeed the Applicant has found, that the structure of the foam allows controlling the packing density of the cleaning particles, wherein said packing density demonstrates to be important factor for the cleaning performance of the particles.

It is understood that the foam structure parameters described below have a direct impact on the packing density after grinding of the foam into abrasive particles; hence the accurate control of the foam structure is a preferred and convenient way to synthesized efficient abrasive particles.

In a highly preferred embodiment herein, in order to achieve derided packing density of the abrasive cleaning particles, the abrasive cleaning particles are obtained from foamed polymeric material, which is reduced into the abrasive particles preferably by grinding or milling as described above.

The applicant has found that low packing density particles can be achieved from foams with controlled foam density, foam cell size and struts aspect ratio. Low packing density particles can be produced by foam having density above 100 kg/m$^3$ and even up to 500 kg/m$^3$. However the applicant has found that lower packing density particles can be produced from foam having density below 100 kg/m$^3$, more preferably from 50 kg/m$^3$ to 100 kg/m$^3$ and most preferably from 5 kg/m$^3$ to 50 kg/m$^3$ (ASTM D3574 can be used as protocol to evaluate foam density).

Similarly, low packing density particles can be produced from foams with cell size ranging from 20 micrometers till 2000 micrometers. However the applicant found that lower packing density can be achieved with the foam featuring cell size from 100 micrometers to 1000 micrometers, more preferably from 200 micrometers to 500 micrometers and most preferably from 300 micrometers to 450 micrometers (ASTM D3576 can be used as protocol to evaluate cell size). By the term cell size is meant by the diameter of an imaginary sphere inscribed in the Pentagonal dodecahedron structure of the foam and can be measured with use of the Visiocell software.

Figure 1:
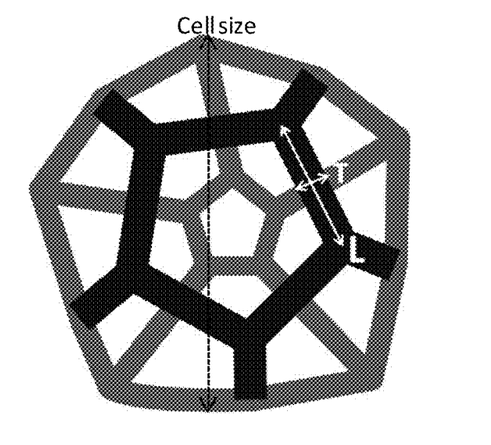
FIG. 1 is an illustration how to calculate foam strut aspect ratio.

FIG. 1 is an illustration of the cell size.

The applicant also found that low packing density particles can be achieved from foams made of struts with high aspect ratio. By struts, meant to define the elongated material that are interconnecting to form the cellular structure of the foam, e.g.: best described as a pentagonal dodecahedron structure for foams with density typically between 5 and 50 kg/m$^3$ targeted herein. The struts length (L) is typically counted as the distance between the geometrical centers of 2 interconnecting knots. The struts thickness (T) is typically the projected strut thickness at the middle of the strut length. The Applicant has understood that particles that are derived from foam presenting struts with excessively small L/T ratio, will present sub-optimal shape for cleaning since likely to produce rounder particle with high rolling. On the contrary, the particles that are derived from foam presenting struts with excessively high L/T ratio will also present sub-optimal shape for cleaning since likely to produce excessive amount of rod-like particles featuring low soil removal. Incidentally, the Applicant have surprisingly found that significantly low packing density particles can be achieved with struts L/T ratio ranging from 1.5 to 10, preferably from 2.0 to 8.0 and more preferably from 3.0 to 6.0 and most preferred from 3.5 to 4.5 as defined by Visiocell software.

FIG. 1 is an illustration of a strut aspect ratio measurement: pentagonal dodecahedron structure with struts length (L) and thickness (T).

The Applicant has found out that no direct correlation can be a priori established between the foamed or expanded material and the packing density of the particles that are derived from the foamed or expanded material unless a careful control of grinding/milling or other similar processes of the foamed/ expanded material is used. Especially, it has been found that excessive reduction of the particle size leads to high packing density and incidentally low cleaning efficiency. Especially, the applicant found that excellent packing density can be achieved by targeting particle size typically above the about half of the foam cell size.

Optional Ingredients

The compositions according to the present invention may comprise a variety of optional ingredients depending on the technical benefit aimed for and the surface treated.

Suitable optional ingredients for use herein include chelating agents, surfactants, radical scavengers, perfumes, surface-modifying polymers, solvents, builders, buffers, bactericides, hydrotropes, colorants, stabilizers, bleaches, bleach activators, suds controlling agents like fatty acids, enzymes, soil suspenders, brighteners, anti dusting agents, dispersants, pigments, and dyes.

Suspending Aid

The abrasive cleaning particles present in the composition herein are solid particles in a liquid composition. Said abrasive cleaning particles may be suspended in the liquid composition. However, it is well within the scope of the present invention that such abrasive cleaning particles are not-stably suspended within the composition and either settle or float on top of the composition. In this case, a user may have to temporally suspend the abrasive cleaning particles by agitating (e.g., shaking or stiffing) the composition prior to use.

However, it is preferred herein that the abrasive cleaning particles are stably suspended in the liquid compositions herein. Thus the compositions herein comprise a suspending aid.

The suspending aid herein may either be a compound specifically chosen to provide a suspension of the abrasive cleaning particles in the liquid compositions of the present invention, such as a structurant, or a compound that also provides another function, such as a thickener or a surfactant (as described herein elsewhere).

Any suitable organic and inorganic suspending aids typically used as gelling, thickening or suspending agents in cleaning/cleansing compositions and other detergent or cosmetic compositions may be used herein. Indeed, suitable organic suspending aids include polysaccharide polymers. In addition or as an alternative, polycarboxylate polymer thickeners may be used herein. Also, in addition or as an alternative of the above, layered silicate platelets e.g.: Hectorite, bentonite or montmorillonites can also be used. Suitable commercially available layered silicates are Laponite RD® or Optigel CL® available from Rockwood Additives.

Suitable polycarboxylate polymer thickeners include (preferably lightly) crosslinked polyacrylate. A particularly suitable polycarboxylate polymer thickener is Carbopol commercially available from Lubrizol under the trade name Carbopol 674®.

Suitable polysaccharide polymers for use herein include substituted cellulose materials like carboxymethylcellulose, ethyl cellulose, hydroxyethyl cellulose, hydroxypropyl cellulose, hydroxymethyl cellulose, succinoglycan and naturally occurring polysaccharide polymers like Xanthan gum, gellan gum, guar gum, locust bean gum, tragacanth gum, succinoglucan gum, or derivatives thereof, or mixtures thereof. Xanthan gum is commercially available from Kelco under the tradename Kelzan T.

Preferably the suspending aid herein is Xanthan gum. In an alternative embodiment, the suspending aid herein is a polycarboxylate polymer thickeners preferably a (preferably lightly) crosslinked polyacrylate. In a highly preferred embodiment herein, the liquid compositions comprise a combination of a polysaccharide polymer or a mixture thereof, preferably Xanthan gum, with a polycarboxylate polymer or a mixture thereof, preferably a crosslinked polyacrylate.

As a preferred example, Xanthan gum is preferably present at levels between 0.1% to 5% by weight of the total composition, more preferably from 0.5% to 2%, even more preferably from 0.8% to 1.2%.

Organic Solvent

As an optional but highly preferred ingredient the composition herein comprises an organic solvents or mixtures thereof.

The compositions herein comprise from 0% to 30% by weight of the total composition of an organic solvent or a mixture thereof, more preferably 1.0% to 20% and most preferably, 2% to 15%.

Suitable solvents can be selected from the group consisting of: aliphatic alcohols, ethers and diethers having from 4 to 14 carbon atoms, preferably from 6 to 12 carbon atoms, and more preferably from 8 to 10 carbon atoms; glycols or alkoxylated glycols; glycol ethers; alkoxylated aromatic alcohols; aromatic alcohols; terpenes; and mixtures thereof. Aliphatic alcohols and glycol ether solvents are most preferred.

Aliphatic alcohols, of the formula R—OH wherein R is a linear or branched, saturated or unsaturated alkyl group of from 1 to 20 carbon atoms, preferably from 2 to 15 and more preferably from 5 to 12, are suitable solvents. Suitable aliphatic alcohols are methanol, ethanol, propanol, isopropanol or mixtures thereof. Among aliphatic alcohols, ethanol and isopropanol are most preferred because of their high vapour pressure and tendency to leave no residue.

Suitable glycols to be used herein are according to the formula HO—$CR_1R_2$—OH wherein R1 and R2 are independently H or a $C_2$-$C_{10}$ saturated or unsaturated aliphatic hydrocarbon chain and/or cyclic. Suitable glycols to be used herein are dodecaneglycol and/or propanediol.

In one preferred embodiment, at least one glycol ether solvent is incorporated in the compositions of the present invention. Particularly preferred glycol ethers have a terminal $C_3$-$C_6$ hydrocarbon attached to from one to three ethylene glycol or propylene glycol moieties to provide the appropriate degree of hydrophobicity and, preferably, surface activity. Examples of commercially available solvents based on ethylene glycol chemistry include mono-ethylene glycol n-hexyl ether (Hexyl Cellosolve®) available from Dow Chemical. Examples of commercially available solvents based on propylene glycol chemistry include the di-, and tri-propylene glycol derivatives of propyl and butyl alcohol, which are available from Arco under the trade names Arcosolv® and Dowanol®.

In the context of the present invention, preferred solvents are selected from the group consisting of mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, and mixtures thereof. "Butyl" includes normal butyl, isobutyl and tertiary butyl groups. Mono-propylene glycol and mono-propylene glycol mono-butyl ether are the most preferred cleaning solvent and are available under the tradenames Dowanol DPnP® and Dowanol DPnB®. Di-propylene glycol mono-t-butyl ether is commercially available from Arco Chemical under the tradename Arcosolv PTB®.

In a particularly preferred embodiment, the cleaning solvent is purified so as to minimize impurities. Such impurities include aldehydes, dimers, trimers, oligomers and other by-products. These have been found to deleteriously affect product odour, perfume solubility and end result. The inventors have also found that common commercial solvents, which contain low levels of aldehydes, can cause irreversible and irreparable yellowing of certain surfaces. By purifying the cleaning solvents so as to minimize or eliminate such impurities, surface damage is attenuated or eliminated.

Though not preferred, terpenes can be used in the present invention. Suitable terpenes to be used herein monocyclic terpenes, dicyclic terpenes and/or acyclic terpenes. Suitable terpenes are: D-limonene; pinene; pine oil; terpinene; terpene derivatives as menthol, terpineol, geraniol, thymol; and the citronella or citronellol types of ingredients.

Suitable alkoxylated aromatic alcohols to be used herein are according to the formula R—(A)$_n$—OH wherein R is an alkyl substituted or non-alkyl substituted aryl group of from 1 to 20 carbon atoms, preferably from 2 to 15 and more preferably from 2 to 10, wherein A is an alkoxy group preferably butoxy, propoxy and/or ethoxy, and n is an integer of from 1 to 5, preferably 1 to 2. Suitable alkoxylated aromatic alcohols are benzoxyethanol and/or benzoxypropanol.

Suitable aromatic alcohols to be used herein are according to the formula R—OH wherein R is an alkyl substituted or non-alkyl substituted aryl group of from 1 to 20 carbon atoms, preferably from 1 to 15 and more preferably from 1 to 10. For example a suitable aromatic alcohol to be used herein is benzyl alcohol.

Surfactants

The compositions herein may comprise a nonionic, anionic, zwitterionic, cationic and amphoteric surfactant or mixtures thereof. Suitable surfactants are those selected from the group consisting of nonionic, anionic, zwitterionic, cationic and amphoteric surfactants, having hydrophobic chains containing from 8 to 18 carbon atoms. Examples of suitable surfactants are described in McCutcheon's Vol. 1: Emulsifiers and Detergents, North American Ed., McCutcheon Division, MC Publishing Co., 2002.

Preferably, the composition herein comprises from 0.01% to 20% by weight of the total composition of a surfactant or a mixture thereof, more preferably from 0.5% to 10%, and most preferably from 1% to 5%.

Non-ionic surfactants are highly preferred for use in the compositions of the present invention. Non-limiting examples of suitable non-ionic surfactants include alcohol alkoxylates, alkyl polysaccharides, amine oxides, block copolymers of ethylene oxide and propylene oxide, fluoro surfactants and silicon based surfactants. Preferably, the aqueous compositions comprise from 0.01% to 20% by weight of the total composition of a non-ionic surfactant or a mixture thereof, more preferably from 0.5% to 10%, and most preferably from 1% to 5%.

A preferred class of non-ionic surfactants suitable for the present invention is alkyl ethoxylates. The alkyl ethoxylates of the present invention are either linear or branched, and contain from 8 carbon atoms to 16 carbon atoms in the hydrophobic tail, and from 3 ethylene oxide units to 25 ethylene oxide units in the hydrophilic head group. Examples of alkyl ethoxylates include Neodol 91-6®, Neodol 91-8® supplied by the Shell Corporation (P.O. Box 2463, 1 Shell Plaza, Houston, Tex.), and Alfonic 810-60® supplied by Condea Corporation, (900 Threadneedle P.O. Box 19029, Houston, Tex.). More preferred alkyl ethoxylates comprise from 9 to 12 carbon atoms in the hydrophobic tail, and from 4 to 9 oxide units in the hydrophilic head group. A most preferred alkyl ethoxylate is $C_{9-11}$ $EO_5$, available from the Shell Chemical Company under the tradename Neodol 91-5®. Non-ionic ethoxylates can also be derived from branched alcohols. For example, alcohols can be made from branched olefin feedstocks such as propylene or butylene. In a preferred embodiment, the branched alcohol is either a 2-propyl-1-heptyl alcohol or 2-butyl-1-octyl alcohol. A desirable branched alcohol ethoxylate is 2-propyl-1-heptyl EO7/AO7, manufactured and sold by BASF Corporation under the tradename Lutensol XP 79/XL 79®.

Another class of non-ionic surfactant suitable for the present invention is alkyl polysaccharides. Such surfactants are disclosed in U.S. Pat. Nos. 4,565,647, 5,776,872, 5,883,062, and 5,906,973. Among alkyl polysaccharides, alkyl polyglycosides comprising five and/or six carbon sugar rings are preferred, those comprising six carbon sugar rings are more preferred, and those wherein the six carbon sugar ring is derived from glucose, i.e., alkyl polyglucosides ("APG"), are most preferred. The alkyl substituent in the APG chain length is preferably a saturated or unsaturated alkyl moiety containing from 8 to 16 carbon atoms, with an average chain length of 10 carbon atoms. $C_8$-$C_{16}$ alkyl polyglucosides are commercially available from several suppliers (e.g., Simusol® surfactants from Seppic Corporation, 75 Quai d'Orsay, 75321 Paris, Cedex 7, France, and Glucopon 220®, Glucopon 225®, Glucopon 425®, Plantaren 2000 N®, and Plantaren 2000 N UP®, from Cognis Corporation, Postfach 13 01 64, D 40551, Dusseldorf, Germany).

Another class of non-ionic surfactant suitable for the present invention is amine oxide. Amine oxides, particularly those comprising from 10 carbon atoms to 16 carbon atoms in the hydrophobic tail, are beneficial because of their strong cleaning profile and effectiveness even at levels below 0.10%. Additionally $C_{10-16}$ amine oxides, especially $C_{12}$-$C_{14}$ amine oxides are excellent solubilizers of perfume. Alternative non-ionic detergent surfactants for use herein are alkoxylated alcohols generally comprising from 8 to 16 carbon atoms in the hydrophobic alkyl chain of the alcohol. Typical alkoxylation groups are propoxy groups or ethoxy groups in combination with propoxy groups, yielding alkyl ethoxy propoxylates. Such compounds are commercially available under the tradename Antarox® available from Rhodia (40 Rue de la Haie-Coq F-93306, Aubervilliers Cédex, France) and under the tradename Nonidet® available from Shell Chemical.

The condensation products of ethylene oxide with a hydrophobic base formed by the condensation of propylene oxide with propylene glycol are also suitable for use herein. The hydrophobic portion of these compounds will preferably have a molecular weight of from 1500 to 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to 40 moles of ethylene oxide. Examples of compounds of this type include certain of the commercially available Pluronic® surfactants, marketed by BASF. Chemically, such surfactants have the structure $(EO)_x(PO)_y(EO)_z$ or $(PO)_x(EO)_y(PO)_z$ wherein x, y, and z are from 1 to 100, preferably 3 to 50. Pluronic® surfactants known to be good wetting surfactants are more preferred. A description of the Pluronic® surfactants, and properties thereof, including wetting properties, can be found in the brochure entitled "BASF Performance Chemicals Plutonic® & Tetronic® Surfactants", available from BASF.

Other suitable though not preferred non-ionic surfactants include the polyethylene oxide condensates of alkyl phenols, e.g., the condensation products of alkyl phenols having an alkyl group containing from 6 to 12 carbon atoms in either a straight chain or branched chain configuration, with ethylene oxide, the said ethylene oxide being present in amounts equal to 5 to 25 moles of ethylene oxide per mole of alkyl phenol. The alkyl substituent in such compounds can be derived from oligomerized propylene, diisobutylene, or from other sources of iso-octane n-octane, iso-nonane or n-nonane. Other non-ionic surfactants that can be used include those derived from natural sources such as sugars and include $C_8$-$C_{16}$ N-alkyl glucose amide surfactants.

Suitable anionic surfactants for use herein are all those commonly known by those skilled in the art. Preferably, the anionic surfactants for use herein include alkyl sulphonates, alkyl aryl sulphonates, alkyl sulphates, alkyl alkoxylated sulphates, $C_6$-$C_{20}$ alkyl alkoxylated linear or branched diphenyl oxide disulphonates, or mixtures thereof.

Suitable alkyl sulphonates for use herein include water-soluble salts or acids of the formula $RSO_3M$ wherein R is a $C_6$-$C_{20}$ linear or branched, saturated or unsaturated alkyl group, preferably a $C_8$-$C_{18}$ alkyl group and more preferably a $C_{10}$-$C_{16}$ alkyl group, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like).

Suitable alkyl aryl sulphonates for use herein include water-soluble salts or acids of the formula $RSO_3M$ wherein R is an aryl, preferably a benzyl, substituted by a $C_6$-$C_{20}$ linear or branched saturated or unsaturated alkyl group, preferably a $C_8$-$C_{18}$ alkyl group and more preferably a $C_{10}$-$C_{16}$ alkyl group, and M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like).

An example of a $C_{14}$-$C_{16}$ alkyl sulphonate is Hostapur® SAS available from Hoechst. An example of commercially available alkyl aryl sulphonate is Lauryl aryl sulphonate from Su.Ma. Particularly preferred alkyl aryl sulphonates are alkyl benzene sulphonates commercially available under trade name Nansa® available from Albright&Wilson.

Suitable alkyl sulphate surfactants for use herein are according to the formula $R_1SO_4M$ wherein $R_1$ represents a hydrocarbon group selected from the group consisting of straight or branched alkyl radicals containing from 6 to 20 carbon atoms and alkyl phenyl radicals containing from 6 to 18 carbon atoms in the alkyl group. M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like). Particularly preferred branched alkyl sulphates to be used herein are those containing from 10 to 14 total carbon atoms like Isalchem 123 AS®. Isalchem 123 AS® commercially available from Enichem is a $C_{12-13}$ surfactant which is 94% branched. This material can be described as $CH_3$—$(CH_2)_m$—$CH(CH_2OSO_3Na)$—$(CH_2)_n$—$CH_3$ where n+m=8-9. Also preferred alkyl sulphates are the alkyl sulphates where the alkyl chain comprises a total of 12 carbon atoms, i.e., sodium 2-butyl octyl sulphate. Such alkyl sulphate is commercially available from Condea under the trade name Isofol® 12S. Particularly suitable liner alkyl sulphonates include $C_{12}$-$C_{16}$ paraffin sulphonate like Hostapur® SAS commercially available from Hoechst.

Suitable alkyl alkoxylated sulphate surfactants for use herein are according to the formula $RO(A)_mSO_3M$ wherein R is an unsubstituted $C_6$-$C_{20}$ alkyl or hydroxyalkyl group having a $C_6$-$C_{20}$ alkyl component, preferably a $C_{12}$-$C_{20}$ alkyl or hydroxyalkyl, more preferably $C_{12}$-$C_{18}$ alkyl or hydroxyalkyl, A is an ethoxy or propoxy unit, m is greater than zero, typically between 0.5 and 6, more preferably between 0.5 and 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperidinium and cations derived from alkanolamines such as ethylamine, diethylamine, triethylamine, mixtures thereof, and the like. Exemplary surfactants are $C_{12}$-$C_{18}$ alkyl polyethoxylate (1.0) sulfate ($C_{12}$-$C_{18}E(1.0)SM$), $C_{12}$-$C_{18}$ alkyl polyethoxylate (2.25) sulfate ($C_{12}$-$C_{18}E(2.25)SM$), $C_{12}$-$C_{18}$ alkyl polyethoxylate (3.0) sulfate ($C_{12}$-$C_{18}E(3.0)SM$), $C_{12}$-$C_{18}$ alkyl polyethoxylate (4.0) sulfate ($C_{12}$-$C_{18}E(4.0)SM$), wherein M is conveniently selected from sodium and potassium.

Suitable $C_6$-$C_{20}$ alkyl alkoxylated linear or branched diphenyl oxide disulphonate surfactants for use herein are according to the following formula:

wherein R is a $C_6$-$C_{20}$ linear or branched, saturated or unsaturated alkyl group, preferably a $C_{12}$-$C_{18}$ alkyl group and more preferably a $C_{14}$-$C_{16}$ alkyl group, and X+ is H or a cation, e.g., an alkali metal cation (e.g., sodium, potassium, lithium, calcium, magnesium and the like). Particularly suitable $C_6$-$C_{20}$ alkyl alkoxylated linear or branched diphenyl oxide disulphonate surfactants to be used herein are the $C_{12}$ branched di phenyl oxide disulphonic acid and $C_{16}$ linear di phenyl oxide disulphonate sodium salt respectively commercially available by DOW under the trade name Dowfax 2A1® and Dowfax 8390®.

Other anionic surfactants useful herein include salts (including, for example, sodium, potassium, ammonium, and substituted ammonium salts such as mono-, di- and triethanolamine salts) of soap, $C_8$-$C_{24}$ olefinsulfonates, sulphonated polycarboxylic acids prepared by sulphonation of the pyrolyzed product of alkaline earth metal citrates, e.g., as described in British patent specification No. 1,082,179, $C_8$-$C_{24}$ alkylpolyglycolethersulfates (containing up to 10 moles of ethylene oxide); alkyl ester sulfonates such as $C_{14}$-$C_{16}$ methyl ester sulfonates; acyl glycerol sulfonates, fatty oleyl glycerol sulfates, alkyl phenol ethylene oxide ether sulfates, alkyl phosphates, isethionates such as the acyl isethionates, N-acyl taurates, alkyl succinamates and sulfosuccinates, monoesters of sulfosuccinate (especially saturated and unsaturated $C_{12}$-$C_{18}$ monoesters) diesters of sulfosuccinate (especially saturated and unsaturated $C_6$-$C_{14}$ diesters), acyl sarcosinates, sulfates of alkylpolysaccharides such as the sulfates of alkylpolyglucoside (the nonionic nonsulfated compounds being described below), alkyl polyethoxy carboxylates such as those of the formula $RO(CH_2CH_2O)_kCH_2COO^-M^+$ wherein R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Zwitterionic surfactants represent another class of preferred surfactants within the context of the present invention.

Zwitterionic surfactants contain both cationic and anionic groups on the same molecule over a wide pH range. The typical cationic group is a quaternary ammonium group, although other positively charged groups like sulfonium and phosphonium groups can also be used. The typical anionic groups are carboxylates and sulfonates, preferably sulfonates, although other groups like sulfates, phosphates and the like, can be used. Some common examples of these detergents are described in the patent literature: U.S. Pat. Nos. 2,082,275, 2,702,279 and 2,255,082.

A specific example of a zwitterionic surfactant is 3-(N-dodecyl-N,N-dimethyl)-2-hydroxypropane-1-sulfonate (Lauryl hydroxyl sultaine) available from the McIntyre Company (24601 Governors Highway, University Park, Ill. 60466, USA) under the tradename Mackam LHS®. Another specific zwitterionic surfactant is $C_{12-14}$ acylamidopropylene (hydroxypropylene) sulfobetaine that is available from McIntyre under the tradename Mackam 50-SB®. Other very useful zwitterionic surfactants include hydrocarbyl, e.g., fatty alkylene betaines. A highly preferred zwitterionic surfactant is Empigen BB®, a coco dimethyl betaine produced by Albright & Wilson. Another equally preferred zwitterionic surfactant is Mackam 35HP®, a coco amido propyl betaine produced by McIntyre.

Another class of preferred surfactants comprises the group consisting of amphoteric surfactants. One suitable amphoteric surfactant is a $C_8$-$C_{16}$ amido alkylene glycinate surfactant ('ampho glycinate'). Another suitable amphoteric surfactant is a $C_8$-$C_{16}$ amido alkylene propionate surfactant ('ampho propionate'). Other suitable, amphoteric surfactants are represented by surfactants such as dodecylbeta-alanine, N-alkyltaurines such as the one prepared by reacting dodecylamine with sodium isethionate according to the teaching of U.S. Pat. No. 2,658,072, N-higher alkylaspartic acids such as those produced according to the teaching of U.S. Pat. No. 2,438,091, and the products sold under the trade name "Miranol®", and described in U.S. Pat. No. 2,528,378.

Chelating Agents

One class of optional compounds for use herein includes chelating agents or mixtures thereof. Chelating agents can be incorporated in the compositions herein in amounts ranging from 0.0% to 10.0% by weight of the total composition, preferably 0.01% to 5.0%.

Suitable phosphonate chelating agents for use herein may include alkali metal ethane 1-hydroxy diphosphonates (HEDP), alkylene poly (alkylene phosphonate), as well as amino phosphonate compounds, including amino aminotri (methylene phosphonic acid) (ATMP), nitrilo trimethylene phosphonates (NTP), ethylene diamine tetra methylene phosphonates, and diethylene triamine penta methylene phosphonates (DTPMP). The phosphonate compounds may be present either in their acid form or as salts of different cations on some or all of their acid functionalities. Preferred phosphonate chelating agents to be used herein are diethylene triamine penta methylene phosphonate (DTPMP) and ethane 1-hydroxy diphosphonate (HEDP). Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987, to Hartman and Perkins. Ethylenediamine N,N'-disuccinic acids is, for instance, commercially available under the tradename ssEDDS® from Palmer Research Laboratories.

Suitable amino carboxylates for use herein include ethylene diamine tetra acetates, diethylene triamine pentaacetates, diethylene triamine pentaacetate (DTPA), N-hydroxyethylethylenediamine triacetates, nitrilotri-acetates, ethylenediamine tetrapropionates, triethylenetetraaminehexa-acetates, ethanol-diglycines, propylene diamine tetracetic acid (PDTA) and methyl glycine di-acetic acid (MGDA), both in their acid form, or in their alkali metal, ammonium, and substituted ammonium salt forms. Particularly suitable amino carboxylates to be used herein are diethylene triamine penta acetic acid, propylene diamine tetracetic acid (PDTA) which is, for instance, commercially available from BASF under the trade name Trilon FS® and methyl glycine di-acetic acid (MGDA).

Further carboxylate chelating agents for use herein include salicylic acid, aspartic acid, glutamic acid, glycine, malonic acid or mixtures thereof.

Radical Scavenger

The compositions of the present invention may further comprise a radical scavenger or a mixture thereof.

Suitable radical scavengers for use herein include the well-known substituted mono and dihydroxy benzenes and their analogs, alkyl and aryl carboxylates and mixtures thereof. Preferred such radical scavengers for use herein include di-tert-butyl hydroxy toluene (BHT), hydroquinone, di-tert-butyl hydroquinone, mono-tert-butyl hydroquinone, tert-butyl-hydroxy anysole, benzoic acid, toluic acid, catechol, t-butyl catechol, benzylamine, 1,1,3-tris(2-methyl-4-hydroxy-5-t-butylphenyl) butane, n-propyl-gallate or mixtures thereof and highly preferred is di-tert-butyl hydroxy toluene. Such radical scavengers like N-propyl-gallate may be commercially available from Nipa Laboratories under the trade name Nipanox S1®.

Radical scavengers, when used, may be typically present herein in amounts up to 10% by weight of the total composition and preferably from 0.001% to 0.5%. The presence of radical scavengers may contribute to the chemical stability of the compositions of the present invention.

Perfume

Suitable perfume compounds and compositions for use herein are for example those described in EP-A-0 957 156 under the paragraph entitled "Perfume", on page 13. The compositions herein may comprise a perfume ingredient, or mixtures thereof, in amounts up to 5.0% by weight of the total composition, preferably in amounts of 0.1% to 1.5%.

Dye

The liquid compositions according to the present invention may be coloured. Accordingly, they may comprise a dye or a mixture thereof.

Delivery Form of the Compositions

The compositions herein may be packaged in a variety of suitable packaging known to those skilled in the art, such as plastic bottles for pouring liquid compositions, squeeze bottles or bottles equipped with a trigger sprayer for spraying liquid compositions. Alternatively, the paste-like compositions according to the present invention may by packaged in a tube.

In an alternative embodiment herein, the liquid composition herein is impregnated onto a substrate, preferably the substrate is in the form of a flexible, thin sheet or a block of material, such as a sponge.

Suitable substrates are woven or non-woven sheets, cellulosic material based sheets, sponge or foam with open cell structures e.g.: polyurethane foams, cellulosic foam, melamine foam, etc.

The Process of Cleaning a Surface

The present invention encompasses a process of cleaning and/or cleansing a surface with a liquid composition according to the present invention. Suitable surfaces herein are described herein above under the heading "The liquid cleaning/cleansing composition".

In a preferred embodiment said surface is contacted with the composition according to the present invention, preferably wherein said composition is applied onto said surface.

In another preferred embodiment, the process herein comprises the steps of dispensing (e.g., by spraying, pouring, squeezing) the liquid composition according to the present invention from a container containing said liquid composition and thereafter cleaning and/or cleansing said surface.

The composition herein may be in its neat form or in its diluted form.

By "in its neat form", it is to be understood that said liquid composition is applied directly onto the surface to be treated without undergoing any dilution, i.e., the liquid composition herein is applied onto the surface as described herein.

By "diluted form", it is meant herein that said liquid composition is diluted by the user typically with water. The liquid composition is diluted prior to use to a typical dilution level of up to 10 times its weight of water. A usually recommended dilution level is a 10% dilution of the composition in water.

The composition herein may be applied using an appropriate implement, such as a mop, paper towel, brush (e.g., a toothbrush) or a cloth, soaked in the diluted or neat composition herein. Furthermore, once applied onto said surface said composition may be agitated over said surface using an appropriate implement. Indeed, said surface may be wiped using a mop, paper towel, brush or a cloth.

The process herein may additionally contain a rinsing step, preferably after the application of said composition. By "rinsing", it is meant herein contacting the surface cleaned/cleansed with the process according to the present invention with substantial quantities of appropriate solvent, typically water, directly after the step of applying the liquid composition herein onto said surface. By "substantial quantities", it is meant herein between 0.01 l and 1 l of water per m² of surface, more preferably between 0.1 l and 1 l of water per m² of surface.

In a highly preferred embodiment herein, process of cleaning is a process of cleaning household hard surfaces with a liquid composition according to present invention.

Cleaning Effectiveness

Cleaning Effectiveness Test Method:

The tiles (typically glossy, white, ceramic 24 cm×4 cm) are covered with 0.3 g of typical greasy soap scum soils mainly based on calcium stearate and artificial body soils commercially available (applied to the tile via a sprayer). The soiled tiles are then dried in an oven at a temperature of 140° C. for 10-45 minutes, preferably 40 minutes and then aged between 2 and 12 hours at room temperature (around 20° C.) in a controlled environment humidity (60-85% RH, preferably 75% RH). Then the soiled tiles are cleaned using 5 ml of the composition of the present invention poured directly on a Spontex® cellulose sponge pre-wetted with water. The sponge is then mounted on a Wet Abrasion Scrub Tester Instrument (such as made by Sheen Instruments Ltd. Kingston, England) with the particle composition coated side facing the tile. The abrasion tester can be configured to supply pressure (e.g. 600 g), and move the sponge over the test surface with a set stroke length (e.g. 30 cm), at set speed (e.g. 37 strokes per minute). The ability of the composition to remove greasy soap scum is measured through the number of strokes needed to perfectly clean the surface, as determined by visual assessment. The lower the number of strokes, the higher the greasy soap scum cleaning ability of the composition.

Cleaning data below achieved with 1% of Abrasive particles in cleaner. Note Abrasive particles used to generate the example cleaning data were made from polyurethane foam having a HV Vickers hardness of 7 kg/mm²

Impact of Foam Structure:

| Foams | Foam Density (kg/m3) | Particle size range (selection via air sieving) | Particle Packing density (kg/m3) | CLEANING INDEX* |
|---|---|---|---|---|
| Polyurethane foam type 2 | 44 | 250-355 μm | 57 | 100% |
| Polyurethane foam type 2 | 33 | 250-355 μm | 59 | 108% |
| REF (Polyurethane foam type 1) | 33 | 250-355 μm | 60 | 100% |
| Polyurethane foam type 3 | 35 | 250-355 μm | 62 | 83% |
| Polyurethane foam type 2 | 43 | 250-355 μm | 63 | 97% |
| Polyurethane foam type 4 | 48 | 250-355 μm | 66 | 119% |
| Polyurethane foam type 2 | 43 | 250-355 μm | 66 | 92% |
| Polyurethane foam type 2 | 60 | 250-355 μm | 68 | 103% |
| Polyurethane foam type 3 | 36 | 250-355 μm | 71 | 94% |
| Polyurethane foam type 2 | 48 | 250-355 μm | 72 | 84% |
| Polyurethane foam type 2 | 45 | 250-355 μm | 75 | 95% |
| Polyurethane foam type 2 | 44 | 250-355 μm | 79 | 108% |
| Polyurethane foam type 3 | 59 | 250-355 μm | 83 | 96% |
| Polyurethane foam type 2 | 55 | 250-355 μm | 88 | 98% |
| Polyurethane foam type 3 | 53 | 250-355 μm | 89 | 80% |
| Polyurethane foam type 3 | 54 | 250-355 μm | 96 | 72% |
| Polyurethane foam type 2 | 52 | 250-355 μm | 96 | 110% |
| Polyurethane foam type 2 | 58 | 250-355 μm | 98 | 100% |
| Polyurethane foam type 3 | 36 | 250-355 μm | 101 | 98% |
| Polyurethane foam type 1 | 60 | 250-355 μm | 116 | 97% |
| Polyurethane foam type 3 | 62 | 250-355 μm | 146 | 81% |
| Polyurethane foam type 1 | 30 | <100 μm | 205 | 43% |
| Polyurethane foam type 3 | 60 | 250-355 μm | 212 | 51% |
| Polyurethane foam type 3 | 71 | 250-355 μm | 228 | 51% |
| Polyurethane foam type 1 | 60 | <100 μm | 228 | 45% |
| Polyurethane foam type 3 | 65 | 250-355 μm | 293 | 48% |
| Polyurethane foam type 3 | 61 | 250-355 μm | 324 | 58% |
| Polyurethane foam type 3 | 74 | 250-355 μm | 342 | 30% |

*Cleaning index are measured using a 1% abrasive particle load in cleaner - Cleaning index as a fraction of cleaning power toward cleaning Greasy Soap Scum. Our lowest packing density material is taken a reference (100%). Particles are made from 4 different formulations for the manufacture of rigid polyurethane foams. Particle HV Vickers hardness is 7 kg/mm².

| Natural particle | Particle size range (selection via air sieving) | Particle Packing density (kg/m3) | # strokes to clean* |
|---|---|---|---|
| Arbocel C 120 (wood flour from Rettenmeier) | 300-500 μm fiber | 175 | 35.1 |
| Lignocel BK 40-90 (wood flour from Rettenmeier) | 300-500 μm fiber | 189 | 30.6 |
| Arbocel C 320 (wood flour from Rettenmeier) | 300-500 μm fiber | 192 | 32.8 |

*Number of strokes to clean Greasy Soap Scum with 3% particle load in cleaner

| Natural particle | Particle size range (selection via air sieving) | Particle Packing density (kg/m3) | # strokes to clean* |
|---|---|---|---|
| Kenaf powder (from Engage NRC) | 250-355 μm | 198 | 19.5 |
| Walnut shell powder | <150 μm | 279 | 26 |
| Pecan shell | 200 μm | 324 | 26 |
| Rice bran powder | <50 μm | 473 | 46 |
| Calcium Sulfate dihydrate | <50 μm | 512 | 38.5 |
| Calcium Carbonate powder | <50 μm | 615 | 30.5 |

*Number of strokes to clean Greasy Soap Scum with 3% particle load in cleaner

Surface Safety

Surface Damage Method:

To measure the surface damage produced by the test particles, mix 0.2 g of the abrasive particles to be tested, with 4 g of an aqueous lotion of NEODOL C9-11 E08 surfactant (Shell Chemicals) (3% surfactant by weight). Wet a new cellulose kitchen sponge (such as Spontex®) of dimensions 4 cm×8.5 cm (and 4.5 cm thick) with 24 ml of distilled or deionised water, then load by uniformly distributing the surfactant and particle mixture over one 4 cm×8.5 cm side of the sponge. The sponge is then mounted on a Wet Abrasion Scrub Tester Instrument (such as made by Sheen Instruments Ltd, Kingston, England) with the particle and surfactant coated side facing the test surface. The test surface to be used should be a new sheet of uncolored, transparent, virgin Poly(methyl methacrylate) (also known as PMMA, Plexiglass, Perspex, Lucite), having a Vickers HV Hardness Value of 25 kg/square mm (+/−2) (as measured using standard test method ISO 14577). The abrasion tester should be configured to supply 600 g of pressure and move the sponge over the test surface with a stroke length of 30 cm, at a speed of 37 strokes per minute. The wet abrasion scrub tester is should be allowed to execute 1,000 strokes (i.e.: 1,000 single-direction displacements), then the sponge is re-loaded with an additional 0.2 g of abrasive and 4 g of surfactant lotion. No additional water should be applied when re-loading the sponge.

The sponge is to be reloaded in this manner every 1,000 strokes, for ten consecutive loadings (i.e., 10,000 strokes in total per test surface). Assessment of damage to the test surface is conducted after 10,000 strokes have been completed. The sponge should not be replaced during the test unless it becomes damaged such as torn or ripped. In which case a new sponge should be wetted, loaded and installed as per instructions for the original sponge, in order to complete the test.

To assess surface damage on the Poly(methyl methacrylate) test surface, visual grading is conducted according to the following 5-level surface damage grading scale: 0=I see no scratches; 1=I think I see scratches; 2=I definitely see small scratches; 3=I see lots of scratches; 4=I see a lot of damage. The Visual Damage Grade is the average of the grades given by 5 independent graders.

Additionally, the surface damage on the Poly(methyl methacrylate) test surface is also assessed by measuring Roughness of the sponge-abraded surface, using a Roughness Tester such as the TR 200 (PortableTesters.com LLC). Several profile roughness parameters are measured, including: average maximum height (Rz); total peak-to-valley height (Rt); Maximum peak height (Rp); maximum valley depth (Rv); mean spacing of irregularities (RSm); and skewness (Rsk).

| Surface damage assessment | No particle | Low packing density particle | Medium packing density particle |
|---|---|---|---|
| Packing density | NA | 60 kg/m3 | 285 kg/m3 |
| Size selection (via air sieving) | NA | 250-125 μm | 250-125 μm |
| # strokes for cleaning (1% load in cleaner) | No clean | 21 | 70 |
| Visual damage grade | 0 | 0.4 | 2.7 |
| Roughness parameter: Rz (Average maximum Height of profile) | 0.079 μm | 0.130 μm | 0.271 μm |
| Roughness parameter: Rt (total peak-to-valley height) | 0.186 μm | 0.413 μm | 0.906 μm |
| Roughness parameter: Rp (Maximum Profile Peak Height) | 0.061 μm | 0.091 μm | 0.154 μm |
| Roughness parameter: Rv (Maximum Profile Valley Depth) | 0.019 μm | 0.040 μm | 0.117 μm |
| Roughness parameter: RSm (Mean Spacing of Profile Irregularities) | 7.0833 mm | 4.3055 mm | 2.2685 mm |
| Roughness parameter: Rsk (Skewness of profil) | 2.839 | 3.065 | 4.5 |

*Note Abrasive particle made from polyurethane foam with HV Vickers hardness of 7 kg/mm$^2$.

EXAMPLES

These following compositions were made comprising the listed ingredients in the listed proportions (weight %). Examples 1-43 herein are met to exemplify the present invention, but are not necessarily used to limit or otherwise define the scope of the present invention.

Abrasive particle used in the examples below were ground from rigid polyurethane foam (controlled foam structure e.g.: foam density, cell size, strut aspect ratio and % cell size content). Polyurethane foam is synthesized from reaction of a diisocyanate (e.g.: base on polymeric methylene diphenyl diisocyanate) and polyols (e.g.: polyether or polyester-based polyol). Wherein the diisocyanate is for example Lupranate M200R from BASF and the polyol is for example Lupranol 3423 from BASF. Foam were ground into small particles and sieved using a rotary mill and particle selection was done with used of air jet sieving instrument from Retsch.

Hard Surface Cleaner Bathroom Composition:

| % Weight | 1 | 2 | 3 |
|---|---|---|---|
| C9-C11 EO8 (Neodol 91-8 ®) | 3 | 2.5 | 3.5 |
| Alkyl Benzene sulfonate | | 1 | |
| C12-14-dimethyl Aminoxide | | 1 | |
| n-Butoxy Propoxy Propanol | | 2 | 2.5 |
| Hydrogene Peroxide | 3 | | |
| Hydrophobic ethoxylated polyurethane (Acusol 882 ®) | 1.5 | 1 | 0.8 |
| Lactic Acid | 3 | | 3.5 |
| Citric Acid | | 3 | 0.5 |
| Polysaccharide (Xanthan Gum, Keltrol CG-SFT ® Kelco) | 0.25 | 0.25 | 0.25 |
| Perfume | 0.35 | 0.35 | 0.35 |
| Abrasive particles having packing density of 60 kg/m³ | 1 | 1 | 1 |
| Water | Balance | Balance | Balance |

Hard Surface Cleaner Bathroom Composition (Cont.):

| % Weight | 4 | 5 | 6 |
|---|---|---|---|
| Chloridric acid | 2 | | |
| Linear C10 alkyl sulphate | 1.3 | 2 | 3 |
| n-Butoxy Propoxy Propanol | 2 | | 1.75 |
| Citric Acid | | 3 | 3 |
| PolyvinylPyrrolidone (Luviskol K60 ®) | 0.1 | 0.1 | 0.1 |
| NaOH | | 0.2 | 0.2 |
| Perfume | 0.4 | 0.4 | 0.4 |
| Polysaccharide (Xanthan Gum Kelzan T ®, Kelco) | 0.3 | 0.35 | 0.35 |
| Abrasive particles having packing density of 60 kg/m³ | 2 | 2 | 2 |
| Water | Balance | Balance | Balance |

Hand-dishwashing Detergent Compositions:

| % Weight | 7 | 8 | 9 |
|---|---|---|---|
| N-2-ethylhexyl sulfocuccinamate | 3 | 3 | 3 |
| C11EO5 | 7 | 14 | |
| C11-EO7 | | | 7 |
| C10-EO7 | 7 | | 7 |
| Trisodium Citrate | 1 | 1 | 1 |
| Potassium Carbonate | 0.2 | 0.2 | 0.2 |
| Perfume | 1 | 1 | 1 |
| Polysaccharide (Xanthan Gum Kelzan T ®, Kelco) | 0.35 | 0.35 | 0.35 |
| Abrasive particles having packing density of 60 kg/m³ | 2 | 2 | 2 |
| Water (+minor e.g.; pH adjusted to 10.5) | Balance | Balance | Balance |

General Degreaser Composition:

| % Weight | 10 | 11 |
|---|---|---|
| C9-C11 EO8 (Neodol 91-8 ®) | 3 | 3 |
| N-Butoxy Propoxy Propanol | 15 | 15 |
| Ethanol | 10 | 5 |
| Isopropanol | | 10 |
| Polysaccharide (Xanthan Gum-glyoxal modified Optixan-T) | 0.35 | 0.35 |
| Abrasive particles having packing density of 60 kg/m³ | 1 | 1 |
| Water (+minor e.g.; pH adjusted to alkaline pH) | Balance | Balance |

Scouring Composition:

| % Weight | 12 | 13 | 14 |
|---|---|---|---|
| Sodium C13-16 prafin sulfonate | 2.5 | 2.5 | 2.5 |
| C12-14-EO7 (Lutensol AO7 ®) | 0.5 | 0.5 | 0.5 |
| Coconut Fatty Acid | 0.3 | 0.3 | 0.3 |
| Sodium Citrate | 3.3 | 3.3 | 3.3 |
| Sodium Carbonate | 3 | 3 | 3 |
| Orange terpenes | 2.1 | 2.1 | 2.1 |
| Benzyl Alcohol | 1.5 | 1.5 | |
| Polyacrylic acid 1.5 Mw | 0.75 | 0.75 | 0.75 |
| Diatomaceous earth (Celite 499 ® median size 10 μm) | 25 | | |
| Calcium Carbonate (Merk 2066 ® median size 10 μm) | | 25 | |
| Abrasive particles having packing density of 146 kg/m³ | 5 | 5 | 5 |
| Water | Balance | Balance | Balance |

Liquid Glass Cleaner:

| % Weight | 15 | 16 |
|---|---|---|
| Butoxypropanol | 2 | 4 |
| Ethanol | 3 | 6 |
| C12-14 sodium sulphate | 0.24 | |
| NaOH/Citric acid | To pH 10 | |
| Citric Acid | | |
| Abrasive particles having packing density of 205 kg/m³ | 0.5 | 0.5 |
| Water (+minor) | Balance | Balance |

Cleaning Wipe (Body Cleansing Wipe):

| % Weight | 17 | 18 | 19 |
|---|---|---|---|
| C10 Amine Oxide | — | 0.02 | — |
| C12,14 Amine Oxide | 0.4 | — | — |
| Betaine (Rewoteric AM CAS 15 U) | — | — | 0.2 |
| C9,11 A5EO (Neodol E 91.5 ®) | — | 0.1 | — |
| C9,11 A8EO (Neodol E 91.8 ®) | — | — | 0.8 |
| C12,14 A5EO | 0.125 | — | — |
| 2-Ethyl Hexyl Sulphate | — | 0.05 | 0.6 |
| Silicone | 0.001 | 0.003 | 0.003 |
| EtOH | 9.4 | 8.0 | 9.5 |
| Propylene Glycol Butyl Ether | 0.55 | 1.2 | — |
| Geraniol | — | — | 0.1 |
| Citric acid | 1.5 | — | — |
| Lactic acid | — | — | 1.5 |
| Perfume | 0.25 | 0.15 | 0.15 |
| Abrasive particles having packing density of 205 kg/m³ | 5 | 3 | 3 |
| Nonwoven: Spunlace 100% viscose 50gsm (lotion loading fact) | | | (x3.5) |
| Nonwoven: Airlaid walkisoft (70% cellulose, 12% Viscose, 18% binder) 80gsm (lotion loading factor) | | (x3.5) | |
| Carded thermobonded (70% polypropylene, 30% rayon), 70gsm (Lotion loading factor) | (x3.5) | | |

Cleaning Wipe (Body Cleansing Wipe):

| % Weight | 20 |
|---|---|
| Benzalkonioum Chloride (Alkaquat DMB-451 ®) | 0.1 |
| Cocamine Oxide (C10/C16 alkyl dimethyl amine oxide; AO-1214 LP supplied by Procter & Gamble Co.) | 0.5 |
| Pyroglutamic Acid (pidolidone) (2-pyrrolidone-5 carboxylic acid) | 4 |
| Ethanol-denatured 200 proof (SD alcohol 40 ®) | 10 |
| DC Antiform H-10 (dimethicone) | 0.03 |
| Sodium Benzoate | 0.2 |

-continued

| % Weight | 20 |
| --- | --- |
| Tetrasodium EDTA (Hampene 220 ®) | 0.1 |
| Sodium Chloride | 0.4 |
| Perfume | 0.01 |
| Abrasive particles having packing density of 205 kg/m$^3$ | 2 |
| Water and minors | balance |

The above wipes lotion composition is loaded onto a water-insoluble substrate, being a patterned hydroentangled nonwoven substrate having a basis weight of 56 gram per square meter comprising 70% polyester and 30% rayon approximately 6.5 inches wide by 7.5 inches long with a caliper of about 0.80 mm Optionally, the substrate can be pre-coated with dimethicone (Dow Corning 200 Fluid 5cst) using conventional substrate coating techniques. Lotion to wipe weight ratio of about 2:1 using conventional substrate coating techniques.

Oral Care Composition (Toothpaste):

| % Weight | 20 | 21 |
| --- | --- | --- |
| Sorbitol (70% sol.) | 24.2 | 24.2 |
| Glycerin | 7 | 7 |
| Carboxymethylcellulose | 0.5 | 0.5 |
| PEG-6 | 4 | 4 |
| Sodium Fluoride | 0.24 | 0.24 |
| Sodium Saccharine | 0.13 | 0.13 |
| Mono Sodium phosphate | 0.41 | 0.41 |
| Tri Sodium phosphate | 0.39 | 0.39 |
| Sodium Tartrate | 1 | 1 |
| TiO2 | 0.5 | 0.5 |
| Silica | 35 | |
| Sodium lauroyl sarcosinate (95% active) | 1 | 1 |
| Flavor | 0.8 | 0.8 |
| Abrasive particles having packing density of 228 kg/m$^3$ | 2 | 5 |
| Water | Balance | Balance |

Body Cleansing Composition:

| % Weight | 22 | 23 |
| --- | --- | --- |
| Cocoamidopropyl betaine | 5.15 | 5.15 |
| Sodium Laureth sulfate | 5.8 | 5.8 |
| Sodium Lauroyl sarcosinate | 0.5 | 0.5 |
| Polyquaternium 10 | 0.1 | 0.1 |
| C12-14 fatty alcohol | 0.45 | 0.45 |
| Zinc Stearate | 1.5 | 1.5 |
| Glycol DiStearate | 0.25 | 0.25 |
| Sodium lauryl sulfate | 0.53 | 0.53 |
| Cocamidopropyl betaine | 0.17 | 0.17 |
| Lauramide Diethanolamide | 0.48 | 0.48 |
| Sodium sulfate | 0.05 | 0.05 |
| Citric Acid | 0.05 | 0.05 |
| DMDM hydantoin (1,3-Dimethylol-5,5-dimethylhydantoin Glydant) | 0.2 | 0.2 |
| Tetra Sodium EDTA | 0.1 | 0.1 |
| Fragance | 0.5 | 0.5 |
| Polysaccharide (Xanthan Gum-glyoxal modified Optixan-T) | 0.2 | 0.2 |
| Abrasive particles having packing density of 212 kg/m$^3$ | 2 | 1 |
| Water and minors | | 1 |
| Water | Balance | Balance |

Facial Cleansing Compositions

| Ingredients | 24 | 25 | 26 | 27 |
| --- | --- | --- | --- | --- |
| Acrylates Copolymer[1] | 1.50 | 2.0 | 1.25 | — |
| Acrylates/C$_{10-30}$ alkyl acrylate crosspolymer[2] | — | — | — | 1.0 |
| Sodium Lauryl Sulfate | 2.0 | — | — | — |
| Sodium Laureth Sulfate | 8.0 | — | — | — |
| Ammonium Lauryl Sulfate | — | 6.0 | — | — |
| Sodium Trideceth Sulfate | — | — | 3.0 | 2.5 |
| Sodium Myristoyl Sarcosinate | — | 2.0 | 3.0 | 2.5 |
| Sodium Lauroamphoacetate[3] | — | — | 6.0 | 5.0 |
| Sodium Hydroxide* | pH > 6 | — | — | — |
| Triethanolamine* | — | pH > 6 | — | pH 5.2 |
| Cocamidopropyl Betaine | 4.0 | 7.0 | — | — |
| Glycerin | 4.0 | 5.0 | 2.0 | 2.0 |
| Sorbitol | — | — | 2.0 | 2.0 |
| Salicylic Acid | — | — | 2.0 | 2.0 |
| Fragrance | 0.1 | 0.1 | 0.1 | 0.1 |
| Preservative | 0.3 | 0.3 | 0.15 | 0.15 |
| Abrasive particles having packing density of 228 kg/m$^3$ | 1.0 | 1.0 | 2.0 | 2.0 |
| PEG 120 Methyl Glucose Trioleate[4] | 0.5 | — | 0.25 | 0.25 |
| PEG 150 Pentaerythrityl Tetrastearate[5] | — | 0.40 | — | — |
| Citric Acid** | pH 5.5 | pH 5.5 | pH 5.5 | pH 5.5 |
| Water | QS to 100% | QS to 100% | QS to 100% | QS to 100% |

*per the supplier use directions, the base is used to activate the acrylates copolymer
**acid can be added to adjust the formula to a lower pH
[1] Carbopol Aqua SF-1 ® from Noveon ™, Inc.
[2] Carbopol Ultrez 21 ® from Noveon ™, Inc.
[3] Miranol ® Ultra L32 from Rhodia
[4] Glucamate LT ® from Chemron
[5] Crothix ® from Croda Examples 24 to 27 are made the following way:

Add Carbopol® to de-ionized free water of the formulation. Add all surfactants except cationics and betaines. If the pH is less than 6 then add a neutralizing agent (typically a base i.e., Triethanolamine, sodium hydroxide) to adjust to a pH greater than 6. If necessary, apply gentle heat to reduce viscosity and help minimize air entrapment. Add betaine and/or cationic surfactants. Add conditioning agents, additional rheology modifiers, pearlizing agents, encapsulated materials, exfoliants, preservatives, dyes, fragrances, abrasive particles and other desirable ingredients. Lastly, if desired reduce the pH with an acid (i.e. citric acid) and increase viscosity by adding sodium chloride.

Oral Care Composition (Toothpaste)

| | 28 | 29 | 30 | 31 | 32 |
| --- | --- | --- | --- | --- | --- |
| Sodium Gluconate | 1.064 | 1.064 | 1.064 | 1.064 | 0.600 |
| Stannous fluoride | 0.454 | 0.454 | 0.454 | 0.454 | 0.454 |
| Sodium fluoride | | | | | |
| Sodium monofluorophosphate | | | | | |
| Zinc Lactate | 0.670 | 0.670 | 0.670 | 0.670 | 2.500 |
| Glycerin | — | — | — | — | 36.000 |
| Polyethylene glycol 300 | | | | | 7.000 |
| Propylene Glycol | | | | | 7.000 |
| Sorbitol (LRS) USP | 39.612 | 39.612 | 39.612 | 39.612 | — |
| Sodium lauryl sulfate solution (28%) | 5.000 | 5.000 | 5.000 | 5.000 | 3.500 |
| Abrasive particles having packing density of 228 kg/m$^3$ | 10.000 | 10.000 | 1.000 | 5.000 | 5.000 |
| Zeodent 119 | — | — | — | — | |
| Zeodent 109 | | | 10.000 | 10.000 | 10.000 |
| Hydrogen peroxide (35% soln) | | | | | |

| | 28 | 29 | 30 | 31 | 32 |
|---|---|---|---|---|---|
| Sodium hexametaphosphate | — | — | — | — | 13.000 |
| Gantrez | — | 2.000 | 2.000 | 2.000 | — |
| Natural CaCO3-600M | — | — | — | — | — |
| Sodium phosphate (mono basic) | — | — | — | — | — |
| Sodium phosphate (Tri basic) | — | — | — | — | 1.000 |
| Zeodent 165 | — | — | — | — | — |
| Cocoamidopropyl Betaine (30% Soln) | — | — | — | — | — |
| Cetyl Alcohol | 3.000 | — | — | — | — |
| Stearyl Alcohol | 3.000 | — | — | — | — |
| Hydroxyethyl cellulose (HEC Natrasol 250M) | — | 0.500 | 0.500 | 0.500 | — |
| CMC 7M8SF | — | 1.300 | 1.300 | 1.300 | — |
| Xanthan Gum | — | — | — | — | 0.250 |
| Poloxamer 407 | — | — | — | — | — |
| Carrageenan mixture | — | 0.700 | 0.700 | 0.700 | 0.600 |
| Titanium dioxide | — | — | — | — | — |
| Saccharin Sodium | 0.500 | 0.500 | 0.500 | 0.500 | 0.500 |
| Flavor | 1.000 | 1.000 | 1.000 | 1.000 | 1.000 |
| Water | QS | QS | QS | QS | QS |

Zeodent 119, 109 and 165 are precipitated silica materials sold by the J. M. Huber Corporation.

Gantrez is a copolymer of maleic anhydride or acid and methyl vinyl ether.

CMC 7M8SF is a sodium carboxymethylcellulose.

Poloxamer is a difunctional block-polymer terminating in primary hydroxyl groups.

| | 33 | 34 | 35 | 36 | 37 |
|---|---|---|---|---|---|
| Sodium Gluconate | — | — | — | — | — |
| Stannous fluoride | — | — | — | — | — |
| Sodium fluoride | — | 0.243 | 0.243 | 0.243 | — |
| Sodium monofluorophosphate | 1.10 | — | — | — | — |
| Zinc Lactate | — | — | — | — | — |
| Glycerin | — | — | — | — | 40.000 |
| Polyethylene glycol 300 | — | — | — | — | — |
| Propylene Glycol | — | — | — | — | — |
| Sorbitol (LRS) USP | 24.000 | 42.500 | 42.500 | 42.500 | 30.000 |
| Sodium lauryl sulfate solution (28%) | 4.000 | 4.000 | — | 4.000 | — |
| Abrasive particles having packing density of 228 kg/m$^3$ | 5.000 | 10.000 | 10.000 | 5.000 | 15.000 |
| Zeodent 119 | — | — | — | 10.000 | — |
| Zeodent 109 | — | — | — | — | — |
| Hydrogen peroxide (35% soln) | — | — | — | — | — |
| Sodium hexametaphosphate | — | — | — | — | — |
| Gantrez | — | — | — | — | — |
| Natural CaCO3-600M | 35.00 | — | — | — | — |
| Sodium phosphate (mono basic) | 0.10 | 0.420 | 0.420 | 0.420 | 0.420 |
| Sodium phosphate (Tri basic) | 0.40 | 1.100 | 1.100 | 1.100 | 1.100 |
| Zeodent 165 | 2.00 | — | — | — | 2.000 |
| Cocoamidopropyl Betaine (30% Soln) | — | — | 5.000 | — | — |
| Cetyl Alcohol | 0.000 | — | — | — | — |
| Stearyl Alcohol | 0.000 | — | — | — | — |
| Hydroxyethyl cellulose (HEC Natrasol 250M) | — | 0.500 | 0.500 | 0.500 | — |
| CMC 7M8SF | 1.300 | 1.300 | 1.300 | 1.300 | 1.300 |
| Xanthan Gum | — | — | — | — | — |
| Poloxamer 407 | — | — | — | — | — |
| Carrageenan mixture | — | 0.700 | 0.700 | 0.700 | — |
| Titanium dioxide | — | — | — | — | — |
| Saccharin Sodium | 0.250 | 0.500 | 0.500 | 0.500 | 0.500 |
| Flavor | 1.000 | 1.000 | 1.000 | 1.000 | 1.000 |
| Water | QS | QS | QS | QS | QS |

| | 38 | 39 | 40 |
|---|---|---|---|
| Sodium Gluconate | — | — | 1.500 |
| Stannous fluoride | — | — | 0.454 |
| Sodium fluoride | — | — | — |
| Sodium monofluorophosphate | — | — | — |
| Zinc Lactate | — | — | — |
| Glycerin | 40.000 | 10.000 | 25.000 |
| Polyethylene glycol 300 | 3.000 | — | — |
| Propylene Glycol | — | — | — |
| Sorbitol (LRS) USP | — | 39.612 | — |
| Sodium lauryl sulfate solution (28%) | 5.000 | 4.000 | 4.000 |
| Abrasive particles having packing density of 228 kg/m$^3$ | 15.000 | 5.000 | 5.000 |
| Zeodent 119 | — | — | — |
| Zeodent 109 | — | — | — |
| Hydrogen peroxide (35% soln) | — | 8.570 | 8.570 |
| Sodium hexametaphosphate | 14.000 | — | — |
| Gantrez | — | — | — |
| Natural CaCO3-600M | — | — | — |
| Sodium phosphate (mono basic) | 0.420 | — | — |
| Sodium phosphate (Tri basic) | 1.100 | — | — |
| Zeodent 165 | 2.000 | — | — |
| Cocoamidopropyl Betaine (30% Soln) | — | — | — |
| Cetyl Alcohol | — | 3.000 | — |
| Stearyl Alcohol | — | 3.000 | — |
| Hydroxyethyl cellulose (HEC Natrasol 250M) | — | — | — |
| CMC 7M8SF | 1.000 | — | — |
| Xanthan Gum | 0.300 | — | — |
| Poloxamer 407 | 0.500 | — | 18.000 |
| Carrageenan mixture | — | — | — |
| Titanium dioxide | 0.500 | — | — |
| Saccharin Sodium | 0.500 | 0.500 | 0.500 |
| Flavor | 1.000 | 1.000 | 1.000 |
| Water | QS | QS | QS |

Hair Shampoo

| | 41 | 42 | 43 |
|---|---|---|---|
| Water | q.s. | q.s. | q.s. |
| Polyquaterium 76[1] | 0.25 | — | — |
| Guar, Hydroxylpropyl Trimonium Chloride[2] | — | 0.25 | — |
| Polyquaterium 6[3] | — | — | 0.25 |
| Sodium Laureth Sulfate | 12 | 10.5 | 10.5 |
| Sodium Lauryl Sulfate | — | 1.5 | 1.5 |
| Silicone[4] | 0.75 | 1.00 | 0.5 |
| Cocoamidopropyl Betaine | 3.33 | 3.33 | 3.33 |
| Cocoamide MEA | 1.0 | 1.0 | 1.0 |
| Ethylene Glycol Distearate | 1.50 | 1.50 | 1.50 |
| Abrasive particles having packing density of 228 kg/m$^3$ | 1 | — | 2 |
| Crosslinked PS-DVB (50% DVB 55, mean diameter D(v, 0.9) 75 μm) abrasive cleaning particles | — | 1 | — |
| Fragrance | 0.70 | 0.70 | 0.70 |
| Preservatives, pH & Visc. adjusters | Up to 1% | Up to 1% | Up to 1% |

[1]Copolymer of Acrylamide(AM) and TRIQUAT, MW = 1,000,000; CD = 1.6 meq./gram; Rhodia
[2]Jaguar C500, MW - 500,000, CD = 0.7, Rhodia
[3]Mirapol 100S, 31.5% active, Rhodia
[4]Dimethicone Fluid, Viscasil 330M; 30 micron particle size; Momentive Silicones The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid cleaning and/or cleansing composition comprising
   from about 0.1% to about 20% by weight of the total composition of abrasive cleaning particles,
   from about 65% to about 99.5% by weight of the total composition of water, and
   from about 0.01% to about 20% by weight of the total composition of surfactant, wherein said abrasive cleaning particles have packing density between about 50 kg/m$^3$ and about 150 kg/m$^3$, wherein said abrasive cleaning particles have HV Vickers hardness from about 3 to about 50 kg/mm$^2$, wherein the composition has a pH of about 6.5 to 7.5, and wherein the abrasive particles comprise foamed polymeric material and the foamed polymeric material selected from the group consisting polyethylene, polypropylene, PVC, polycarbonate, melamine, urea, polyurethane, polystyrene, phenolic material, polyesters, polyamide and mixtures thereof.

2. A liquid cleaning and/or cleansing composition according to claim 1, wherein said abrasive cleaning particles have HV Vickers hardness from about 4 to about 25 kg/mm$^2$.

3. A liquid cleaning and/or cleansing composition according to claim 1, wherein said abrasive particles have a mean particle size as expressed by the area-equivalent diameter from about 10 to about 1000 μm.

4. A liquid cleaning and/or cleansing composition according to claim 3 further comprises a suspending aid, wherein said suspending aid is selected from the group consisting of hydroxyl-containing fatty acid wax, hydroxyl-containing fatty ester wax, hydroxyl-containing fatty soap wax carboxymethylcellulose, ethyl cellulose, hydroxyethyl cellulose, hydroxypropyl cellulose, hydroxymethyl cellulose, succinoglycan, Xanthan gum, gellan gum, guar gum, locust bean gum, tragacanth gum, succinoglucan gum and mixtures thereof.

5. A liquid cleaning and/or cleansing composition according to claim 1, wherein said abrasive cleaning particles comprise polyurethane.

6. A liquid cleaning and/or cleansing composition according to claim 5, wherein said abrasive cleaning particles comprise polyurethane foam.

7. A liquid cleaning and/or cleansing composition according to claim 1 whereas the cleaning composition is loaded on a cleaning substrate whereas the substrate is a paper or nonwoven towel or wipe or a sponge.

8. A process of cleaning and/or cleansing a surface with a liquid, cleaning and/or cleansing composition according to claim 1, wherein said surface is contacted with said composition.

9. A process according to claim 7, wherein said surface is an inanimate surface, preferably selected from the group consisting of household hard surfaces; dish surfaces; leather or synthetic leather surfaces; and automotive vehicles surfaces.

10. A process according to claim 7, wherein said surface is an animate surface.

\* \* \* \* \*